United States Patent
Tse et al.

(10) Patent No.: US 10,640,690 B2
(45) Date of Patent: *May 5, 2020

(54) ADHESIVE COMPOSITIONS WITH (METH)ACRYLIC-BASED BLOCK COPOLYMERS

(71) Applicant: 3M INNOVATIVE PROPERTIES COMPANY, St. Paul, MN (US)

(72) Inventors: Kiu-Yuen Tse, Woodbury, MN (US); Michael D. Determan, Mahtomedi, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 25 days.

This patent is subject to a terminal disclaimer.

(21) Appl. No.: 16/082,416

(22) PCT Filed: Mar. 14, 2017

(86) PCT No.: PCT/US2017/022226
§ 371 (c)(1),
(2) Date: Sep. 5, 2018

(87) PCT Pub. No.: WO2017/160785
PCT Pub. Date: Sep. 21, 2017

(65) Prior Publication Data
US 2019/0085222 A1 Mar. 21, 2019

Related U.S. Application Data

(60) Provisional application No. 62/310,382, filed on Mar. 18, 2016.

(51) Int. Cl.
| | | |
|---|---|---|
| C09J 153/00 | (2006.01) | |
| C08L 53/00 | (2006.01) | |
| A61K 9/70 | (2006.01) | |
| C09J 133/08 | (2006.01) | |
| C09J 133/10 | (2006.01) | |

(52) U.S. Cl.
CPC .......... *C09J 153/00* (2013.01); *A61K 9/7061* (2013.01); *C08L 53/00* (2013.01); C08L 2203/02 (2013.01); C08L 2205/02 (2013.01); C08L 2312/06 (2013.01); *C09J 133/08* (2013.01); *C09J 133/10* (2013.01); C09J 2205/114 (2013.01); C09J 2205/31 (2013.01); C09J 2467/005 (2013.01)

(58) Field of Classification Search
CPC ...... C09J 153/00; C09J 133/08; C09J 133/10; C09J 2205/114; C09J 2205/31; C09J 2467/005; C08L 53/00; C08L 2203/02; C08L 2205/02; A61K 9/7061
See application file for complete search history.

(56) References Cited

U.S. PATENT DOCUMENTS

| | | |
|---|---|---|
| 5,711,940 A | 1/1998 | Kuentz |
| 6,723,407 B2 | 4/2004 | Dollase |
| 6,734,256 B1 | 5/2004 | Everaerts |
| 6,806,320 B2 | 10/2004 | Everaerts |
| 7,084,209 B2 | 8/2006 | Everaerts |
| 7,255,920 B2 | 8/2007 | Everaerts |
| 7,384,998 B2 | 6/2008 | Paul |
| 7,714,052 B2 | 5/2010 | Paul |
| 8,129,470 B2 | 3/2012 | Dollase |
| 2011/0135921 A1 | 6/2011 | Tse |
| 2013/0079468 A1 | 3/2013 | Kanemura |
| 2014/0066539 A1 | 3/2014 | Tobing |

FOREIGN PATENT DOCUMENTS

| | | |
|---|---|---|
| EP | 1132410 | 9/2001 |
| EP | 1489116 | 12/2004 |
| EP | 1842888 | 10/2007 |
| EP | 1939262 | 7/2008 |
| EP | 2578655 | 4/2013 |
| JP | 2004300202 A * | 10/2004 |
| JP | 2010155923 | 7/2010 |
| WO | WO 1997-018247 | 5/1997 |
| WO | WO 1998-001478 | 1/1998 |
| WO | WO 2010-056541 | 5/2010 |
| WO | WO 2010-056543 | 5/2010 |
| WO | WO 2010-056544 | 5/2010 |
| WO | WO 2014-035971 | 3/2014 |
| WO | WO 2014-035981 | 3/2014 |
| WO | WO 2016-044378 | 3/2016 |

OTHER PUBLICATIONS

International Search report for PCT International Application No. PCT/US2017/022226 dated Jun. 26, 2017, 4 pages.

* cited by examiner

*Primary Examiner* — Irina S Zemel
*Assistant Examiner* — Jeffrey S Lenihan
(74) *Attorney, Agent, or Firm* — Jean A. Lown

(57) ABSTRACT

Adhesive compositions are provided that contain a crosslink product resulting from exposure of a (meth)acrylic-based composition to electron beam radiation, gamma ray radiation, or both. More particularly, the (meth)acrylic-based composition includes a (meth)acrylic-based diblock copolymer and an optional (meth)acrylic-based triblock copolymer. These adhesive compositions are particularly well suited for application to biological surface such as skin.

11 Claims, No Drawings

ADHESIVE COMPOSITIONS WITH (METH)ACRYLIC-BASED BLOCK COPOLYMERS

CROSS REFERENCE TO RELATED APPLICATIONS

This application is a national stage filing under 35 U.S.C. 371 of PCT/US2017/022226, filed Mar. 14, 2017, which claims the benefit of Provisional Application No. 62/310,382, filed Mar. 18, 2016, the disclosure of which is incorporated by reference in its/their entirety herein.

TECHNICAL FIELD

Adhesive compositions containing (meth)acrylic block copolymers, adhesive articles containing the adhesive compositions, and methods of making the adhesive articles are provided.

BACKGROUND (Meth)acrylic block copolymers have been used to prepare adhesive compositions as described, for example, in EP 1 842 888 A1 (Kasahara et al.), EP 1 489 116 A1 (Morishita et al.), U.S. Pat. No. 8,129,470 (Dollase et al.), US 2013/0079468 (Kanemura et al.), U.S. Pat. No. 7,255,920 (Everaerts et al.), U.S. Pat. No. 6,734,256 (Everaerts et al.), U.S. Pat. No. 6,806,320 (Everaerts et al.), U.S. Pat. No. 7,384,998 (Paul et al.), U.S. Pat. No. 7,714,052 (Paul et al.), and U.S. Pat. No. 6,723,407 (Dollase et al.). While a variety of adhesive compositions are known, not all of them are suitable for application to a biological surface such as skin.

SUMMARY

Adhesive compositions are provided that contain a crosslinked polymeric material resulting from exposure of a (meth)acrylic-based composition to electron beam radiation, gamma ray radiation, or both. More particularly, the (meth)acrylic-based composition includes a (meth)acrylic-based diblock copolymer and an optional (meth)acrylic-based triblock copolymer. These adhesive compositions are particularly well suited for application to biological surface such as skin. For example, the adhesive compositions have sufficient tackiness to adhere rapidly to skin, can be removed easily from skin (i.e., can be removed without pulling excessively (e.g., painfully) on the skin), can be removed cleanly from skin (i.e., can be removed leaving little or no residue), and can adhere to skin with minimal or no edge lift (i.e., the edges of the adhesive article typically remain in contact with the skin during use).

In a first aspect, an adhesive composition is provided that contains a crosslinked polymeric product of (a) a reaction mixture containing a (meth)acrylic-based composition and (b) electron beam radiation and/or gamma ray radiation. The (meth)acrylic-based composition includes (1) 0 to less than 10 weight percent of a (meth)acrylic-based triblock copolymer A-B-A and (2) greater than 90 to 100 weight percent of a (meth)acrylic-based diblock copolymer C-D. The weight percent amounts are based on a total weight of the (meth)acrylic-based composition. The optional (meth)acrylic-based triblock copolymer A-B-A contains 20 to 55 weight percent A blocks and 45 to 80 weight percent B block based on a total weight of the triblock copolymer A-B-A. Each A block is a polymerized product of a first monomer composition comprising an alkyl methacrylate and the B block is a polymerized product of a second monomer composition comprising an alkyl acrylate. The (meth)acrylic-based diblock copolymer C-D contains 5 to 30 weight percent C block and 70 to 95 weight percent D block based on a total weight of the (meth)acrylic-based diblock copolymer C-D. The C block is a polymerized product of a third monomer composition comprising an alkyl methacrylate and the D block is a polymerized product of a fourth monomer composition comprising an alkyl acrylate.

In a second aspect, an adhesive article is provided that includes a substrate and an adhesive composition layer having a first major surface positioned adjacent to the substrate (i.e., the adhesive composition layer is attached directly or indirectly to the substrate). The adhesive composition layer contains the adhesive composition described above.

In a third aspect, a method of making an adhesive article is provided. The method includes providing an adhesive composition comprising a (meth)acrylic-based composition that contains (1) 0 to less than 10 weight percent of a (meth)acrylic-based triblock copolymer A-B-A and (2) greater than 90 to 100 weight percent of a (meth)acrylic-based diblock copolymer C-D. The weight percent amounts are based on a total weight of the (meth)acrylic-based composition. The optional (meth)acrylic-based triblock copolymer A-B-A contains 20 to 55 weight percent A blocks and 45 to 80 weight percent B block based on a total weight of the triblock copolymer A-B-A. Each A block is a polymerized product of a first monomer composition comprising an alkyl methacrylate and the B block is a polymerized product of a second monomer composition comprising an alkyl acrylate. The (meth)acrylic-based diblock copolymer C-D contains 5 to 30 weight percent C block and 70 to 95 weight percent D block based on a total weight of the (meth)acrylic-based diblock copolymer C-D. The C block is a polymerized product of a third monomer composition comprising an alkyl methacrylate and the D block is a polymerized product of a fourth monomer composition comprising an alkyl acrylate. The method further includes forming an adhesive composition layer adjacent to a substrate. The method still further includes exposing the adhesive composition layer to electron beam radiation and/or gamma ray radiation to crosslink the adhesive composition layer.

DETAILED DESCRIPTION

Adhesive compositions, adhesive articles that contain the adhesive compositions, and methods of making the adhesive articles are provided. The adhesive compositions contain a crosslinked polymeric product resulting from exposure of a (meth)acrylic-based composition to electron beam radiation and/or gamma ray radiation. The (meth)acrylic-based composition contains a (meth)acrylic-based diblock copolymer and an optional (meth)acrylic-based triblock copolymer. In some embodiments, the adhesive compositions and adhesive articles are applied to (e.g., adhered to) biological surfaces such as skin. The adhesive compositions and adhesive articles have sufficient tackiness to quickly adhere to skin and sufficient shear strength (e.g., cohesive strength) to allow clean removal of the adhesive compositions and adhesive articles from skin while also adhering sufficiently to skin so that the edges of the adhesive composition and adhesive articles do not undesirably lift away from the skin during use. Further, the adhesive compositions and adhesive articles can be removed without painfully pulling on the skin.

The terms "a", "an", and "the" are used interchangeably with "at least one" to mean one or more of the elements being described.

The term "and/or" means either or both. For example, the expression "X and/or Y" means refers only to X, only to Y, or to both X and Y.

The term "block copolymer" refers to a copolymer having a plurality of different polymeric segments, which are known as "blocks". Each block can be a homopolymer (i.e., a polymeric segment formed from a single type of monomer) or a copolymer (i.e., a polymeric segment formed from multiple (i.e., two or more) different types of monomers). Typically, the block copolymer is either a (meth)acrylic-based triblock copolymer or a (meth)acrylic-based diblock copolymer. The boundary between adjacent blocks in the block copolymer can be sharp (i.e., the composition of the monomeric units changes abruptly at the boundary between two blocks) or tapered (i.e., the composition of the monomeric units does not change abruptly at the boundary between two blocks but is mixed in a transition region near the boundary; the transition region contains monomeric units from both adjacent blocks).

The term "triblock copolymer" refers to a block copolymer having three different polymeric blocks and the term "diblock copolymer" refers to a block copolymer having two different polymeric blocks. Both the triblock copolymer and the diblock copolymer contain polymeric blocks arranged in a linear manner relative to each other. Stated differently, the diblock copolymers and triblock copolymers are not star copolymers, graft copolymers, comb copolymers, dendrimers, or other macromolecules having substantially nonlinear architectures.

The term "(meth)acrylic" refers to a compound having a (meth)acryloyl group of formula $H_2C=CR-(CO)-$ where R is hydrogen or methyl. The compound can be a monomer or a reaction product formed from a monomer having a (meth)acryloyl group such as a monomeric unit, a polymeric block, or a polymeric material. The monomers can be (meth)acrylic acid, (meth)acrylates, (meth)acrylamides, or mixtures thereof. The term "(meth)acrylic" includes both acrylic and methacrylic, the term "(meth)acrylate" includes both acrylate and methacrylate, and the term "(meth)acrylamide" include both acrylamide and methacrylamide.

The term "alkyl" refers to a monovalent radical of an alkane, which is a saturated hydrocarbon. The alkyl group, depending on the number of carbon atoms, can be linear, branched, cyclic, or a mixture thereof (e.g., there can be a cyclic portion as well as a linear or branched portion). The alkyl group often has 1 to 20 carbon atoms, 1 to 18 carbon atoms, 1 to 12 carbon atoms, 1 to 10 carbon atoms, 1 to 6 carbon atoms, or 1 to 4 carbon atoms.

The term "aryl" refers to a monovalent radical of an aromatic compound. The aromatic compound is typically carbocyclic and often contains 6 to 10 carbon atoms. In many embodiments, the aryl is phenyl.

The term "aralkyl" refers to an alkyl group substituted with an aryl group. The alkyl and aryl groups are the same as described above. The alkyl group often has 1 to 6 carbon atoms, or 1 to 4 carbon atoms and the aryl group has 6 to 10 carbon atoms. In many embodiments, the aralkyl is benzyl.

The term "heteroalkyl" refers to a monovalent radical of a heteroalkane, which is a saturated compound having a carbon backbone interrupted with one or more heteroatoms selected from oxygen, nitrogen, or sulfur.

The terms "adhesive" and "adhesive composition" are used interchangeably.

The phrase such as "greater than 90 to 100 weight percent" is equivalent to the phrase "greater than 90 weight percent to 100 weight percent". This means that the range does not include 90 weight percent and does include 100 weight percent.

As used herein, the terms such as "in the range of" and "in an amount of" include the endpoints and all values between the endpoints.

Adhesive compositions suitable for adhesion to biological surfaces such as skin are often formulated differently than adhesives that are useful on other surfaces such as stainless steel, glass, or various polymeric surfaces such as polyester, polypropylene, and polyethylene. Adhesives suitable for application to skin often are formulated to have a relatively low shear strength so that the adhesive compositions can be easily removed without pulling painfully on the skin yet having sufficient tackiness to ensure quick bonding to the biological surface. Low shear strength adhesives, however, typically leave unacceptable levels of residue when removed. Surprisingly, the adhesive compositions described herein leave relatively little residue when removed from skin even though the shear strength is relatively low. Like many other adhesive compositions, however, the adhesives need to have sufficient peel strength so that they can remain adhered to skin for an adequate period of time (e.g., at least 1 day, at least 2 days, at least 3 days, at least 7 days, at least 10 days, or at least 14 days) without lifting away from the skin at the edges. The adhesive compositions described herein can often remain adhered without significant edge lift (i.e., lifting or curling of the edge of the adhesive so that it is not in contact with the adherend) during use.

In a first aspect, an adhesive composition is provided that contains a crosslinked polymeric product of a reaction mixture containing (a) a (meth)acrylic-based composition and (b) electron beam radiation and/or gamma ray radiation. That is, the adhesive composition contains the crosslinked polymeric product resulting from exposure of a (meth)acrylic-based composition to electron beam radiation and/or gamma ray radiation. The (meth)acrylic-based composition includes (1) 0 to less than 10 weight percent of a (meth)acrylic-based triblock copolymer A-B-A and (2) greater than 90 to 100 weight percent of a (meth)acrylic-based diblock copolymer C-D based on a total weight of the (meth)acrylic-based composition. The adhesive composition can further include other optional components such as tackifiers, plasticizers, fillers, or a combination thereof.

Both the (meth)acrylic-based triblock copolymer A-B-A, if present, and the (meth)acrylic-based diblock C-D copolymer are formed predominately from (meth)acrylic-based monomers (i.e., monomers having a (meth)acryloyl group). That is, greater than 50 weight percent, greater than 60 weight percent, greater than 70 weight percent, greater than 80 weight percent, greater than 90 weight percent, greater than 95 weight percent, greater than 98 weight percent, greater than 99 weight percent, or 100 weight percent of the monomers used to form the (meth)acrylic-based triblock copolymer A-B-A and the (meth)acrylic-based diblock C-D copolymer have a (meth)acryloyl group.

Both the (meth)acrylic-based diblock copolymer C-D and the optional (meth)acrylic-based triblock copolymer A-B-A are phase separated copolymers. The composition of the A blocks and the B block of the (meth)acrylic-based triblock copolymer A-B-A are selected to have solubility parameters that are sufficiently different to cause phase separation between the A blocks and the B block. Likewise, the composition of the C block and the D block of the (meth)acrylic-based diblock copolymer C-D are selected to have solubility parameters that are sufficient different to cause phase separation between the C block and the D block. This phase separation can cause the adhesive composition to have a multiphase morphology at temperatures from ambient temperature (e.g., 20° C. to 25° C.) up to about 150° C.

Further, the C block and the D block of the (meth)acrylic-based diblock copolymer C-D are selected to have different glass transition temperatures. Similarly, the A blocks and the B block of the (meth)acrylic-based triblock copolymer A-B-A are selected to have different glass transition temperatures. The A and C blocks are typically selected to have a higher glass transition temperature than the B and D blocks. The A blocks and the C blocks usually are selected to be more rigid than the B and D blocks. The A and C blocks, which can be referred to as "hard" blocks, have a higher glass transition temperature than the B and D blocks, which can be referred to as "soft" blocks. That is, the glass transition temperatures of the A and C blocks are higher than the glass transition temperatures of the B and D blocks. The A and C blocks can be thermoplastic and can provide structural strength and/or shear strength to the adhesive composition. The B and D blocks can be viscous materials and can provide tack and peel strength (adhesive strength) to the adhesive composition.

The term "glass transition temperature", which can be abbreviated "$T_g$," refers to the temperature at which a polymeric material transitions between being in a glassy state to being in a molten or rubbery state. The glass transition temperature can be determined, for example, using Dynamical Mechanical Analysis. The measurements can be conducted using a rheometer in a shear geometry. For example, the polymeric sample can be tested in a parallel plate rheometer by heating from −50° C. to 200° C. at a rate of 2° C./minute and at a frequency of 1 radian/second. The storage modulus (G'), the loss modulus (G"), and tan δ (G"/G') are plotted versus temperature. At very low temperatures (<−50° C.), the entire polymeric material is in a glassy state and is predominately elastic. A precipitous drop is observed in the storage modulus (G') over a temperature range from about −50° C. to about 20° C. or from about −50° C. to about 0° C. A peak in tan δ is observed that is associated with the $T_g$ of the B block of a (meth)acrylic-based triblock copolymer A-B-A or the D block of a (meth)acrylic-based diblock copolymer C-D. That is, the peak occurs at the glass transition temperature of the B block of a (meth)acrylic-based triblock copolymer A-B-A or of the D block of a (meth)acrylic-based diblock copolymer C-D. Above about 50° C., the storage modulus drops due to the onset of polymeric flow and as the glass transition temperature of the A blocks of the (meth)acrylic-based triblock copolymer A-B-A or C block of the (meth)acrylic-based diblock copolymer C-D are exceeded. A steep increase in tan δ is observed that is associated with the $T_g$ of the A blocks or C block. That is, the steep increase in tan δ occurs at the glass transition temperature of the A blocks or C block.

The phase separation resulting from the difference in glass transition temperatures of the various blocks leads to distinct reinforcing A block and C block domains in a matrix of softer B block and D block domains. That is, the adhesive composition can have distinct regions of hard A and C block domains, which can be nanodomains with sizes on the order of nanometers or tens of nanometers, in a matrix of soft B and D block domains. Matrices of soft block domains that have maximum continuity can be achieved by selecting a B block of the (meth)acrylic-based triblock copolymer that is highly compatible with the D block of the (meth)acrylic-based diblock copolymer. Thus, the B block of the (meth) acrylic-based triblock copolymer is often selected to have the same monomeric units as the D block of the (meth)acrylic-based diblock copolymer.

The A blocks of the (meth)acrylic-based triblock copolymer A-B-A and the C block of the (meth)acrylic-based diblock copolymer C-D are typically selected to have a glass transition temperature ($T_g$) equal to at least 50° C. as measured using Dynamic Mechanical Analysis. In some embodiments, the glass transition temperature is at least 70° C., at least 75° C., at least 80° C., at least 90° C., or at least 100° C. The glass transition temperature can be up to 125° C., up to 150° C., up to 175° C., or even up to 200° C. depending on the composition of monomers used to form the A blocks and the C block. Exemplary ranges of glass transition temperatures of the A blocks include 50° C. to 200° C., 50° C. to 175° C., 50° C. to 150° C., 50° C. to 100° C., 75° C. to 200° C., or 75° C. to 150° C.

The B block of the (meth)acrylic-based triblock copolymer A-B-A and the D block of the (meth)acrylic-based diblock copolymer C-D are viscous segments and are typically selected to have a glass transition temperature no greater than 20° C. as measured using Dynamic Mechanical Analysis. In some embodiments, the glass transition temperature is no greater than 10° C., no greater than 5° C., no greater than 0° C., no greater than −10° C., or no greater than −20° C. The glass transition temperature is often at least −50° C., at least −40° C., or at least −30° C. depending on the composition of monomers used to form the B block and the D block. Exemplary ranges for the glass transition temperature of the B and D blocks include −50° C. to 20° C., −50° C. to 10° C., −50° C. to 0° C., and −50° C. to 10° C.

The optional (meth)acrylic-based triblock copolymer A-B-A has two polymeric A blocks and one polymeric B block. Each of these blocks can be a homopolymer or a copolymer (i.e., a random copolymer). If present, the (meth)acrylic-based triblock copolymer A-B-A contains 20 to 55 weight percent A blocks and 45 to 80 weight percent B block based on a total weight of the (meth)acrylic-based triblock copolymer. The (meth)acrylic-based triblock copolymer contains at least 20 weight percent, at least 25 weight percent, at least 30 weight percent, or at least 35 weight percent A block based on the total weight of the (meth)acrylic-based triblock copolymer. The amount of A block can be up to 55 weight percent, up to 50 weight percent, up to 45 weight percent, or up to 40 weight percent based on the total weight of the (meth)acrylic-based triblock copolymer. The (meth)acrylic-based triblock copolymer contains at least 45 weight percent, at least 50 weight percent, at least 55 weight percent, or at least 60 weight percent of the B block based on the total weight of the (meth)acrylic-based triblock copolymer. The amount of the B block can be up to 80 weight percent, up to 75 weight percent, up to 70 weight percent, or up to 65 weight percent based on the total weight of the (meth)acrylic-based triblock copolymer. Together, the weight percent of the A blocks and the weight percent of the B block is equal to 100 weight percent based on the total weight of the (meth)acrylic-based triblock copolymer.

Each of the two A blocks of the (meth)acrylic-based triblock copolymer A-B-A can be about the same weight. That is, the weight ratio of the two A blocks of the (meth) acrylic-based triblock copolymer is often 1:1 or close to 1:1 such as greater than 0.9:1. However, other weight ratios can also be used such as in a range of 0.65:1 to 0.9:1. In many cases, the weight ratio of the two A blocks of the (meth) acrylic-based triblock copolymer is no lower than 0.65:1, 0.7:1, 0.75:1, 0.8:1, 0.85:1, 0.9:1, 0.95:1, 0.98:1, or 0.99:1.

The (meth)acrylic-based diblock copolymer C-D has one polymeric C block and one polymeric D block. Each of the blocks can be a homopolymer or a copolymer (i.e., a random copolymer). The (meth)acrylic-based diblock C-D contains 5 to 30 weight percent C blocks and 70 to 95 weight percent D block based on a total weight of the (meth)acrylic-based diblock copolymer C-D. The (meth)acrylic-based diblock copolymer contains at least 5 weight percent, at least 10 weight percent, or at least 15 weight percent C block based on the total weight of the (meth)acrylic-based diblock copolymer. The amount of the C block can be up to 30 weight percent, up to 25 weight percent, or up to 20 weight percent based on the total weight of the copolymer. The (meth)acrylic-based diblock contains at least 70 weight percent, at least 75 weight percent, or at least 80 weight percent D block based on the total weight of the (meth)acrylic-based diblock copolymer C-D. The (meth)acrylic-based diblock copolymer contains up to 95 weight percent, up to 90 weight percent, or up to 85 weight percent D block based on the total weight of the (meth)acrylic-based diblock copolymer. Together, the weight percent of the C block and the D block is equal to 100 weight percent based on the total weight of the (meth)acrylic-based diblock copolymer.

Each A block of the (meth)acrylic-based triblock copolymer A-B-A and the C block of the (meth)acrylic-based diblock copolymer C-D are typically prepared from a monomer composition that includes an alkyl methacrylate. Stated differently, the A block is a polymeric material that is formed from a first monomer composition that includes an alkyl methacrylate and the C block is a polymeric material that is formed from a third monomer composition that includes an alkyl methacrylate. The alkyl methacrylate included in the first monomeric composition can be the same or different than the alkyl methacrylate included in the third monomeric composition. Suitable alkyl methacrylates for preparing the A blocks and the C block have an alkyl group with 1 to 10 carbon atoms, 1 to 8 carbon atoms, 1 to 6 carbon atoms, 1 to 5 carbon atoms, or 1 to 4 carbon atoms. If the alkyl group has 3 to 5 carbon atoms, it is typically branched. If the alkyl group has 6 to 10 carbon atoms, it is typically cyclic or bicyclic.

Example alkyl methacrylates include methyl methacrylate, ethyl methacrylate, isopropyl methacrylate, isobutyl methacrylate, sec-butyl methacrylate, tert-butyl methacrylate, cyclohexyl methacrylate, methylcyclohexyl methacrylate, 3,3,5-trimethylcyclohexyl methacrylate, and isobornyl methacrylate. These monomers, when polymerized as a homopolymer, have a glass transition temperature equal to at least 50° C.

In some instances, the A blocks and the C blocks are homopolymers and each homopolymer is a poly(alkyl methacrylate). The poly(alkyl methacrylate) A blocks can be the same or different than the poly(alkyl methacrylate) C block. Example poly(alkyl methacrylates) include poly(methyl methacrylate), poly(ethyl methacrylate), poly(isopropyl methacrylate), poly(isobutyl methacrylate), poly(sec-butyl methacrylate), poly(tert-butyl methacrylate), poly(cyclohexyl methacrylate), poly(methylcyclohexyl methacrylate), poly(3,3,5-trimethylcyclohexyl methacrylate), and poly (isobornyl methacrylate).

In addition to the alkyl methacrylate monomers, the first monomer composition used to form the A blocks and the third monomer composition used to form the C block can include other optional monomers provided the resulting polymeric blocks have a glass transition temperature that is equal to at least 50° C. when measured using Dynamic Mechanical Analysis. In some embodiments, the first and/or the third monomer composition can include other (meth) acrylic-based monomers such as alkoxy substituted alkyl methacrylates, aryl methacrylates, aralkyl methacrylates, aryloxy substituted alkyl methacrylate, cyclic alkyl acrylates having a cyclic group with 6 to 10 carbon atoms, bicyclic alkyl acrylates having a bicyclic alkyl group with at least 8 carbon atoms, or a mixture thereof. Many of these monomers, when polymerized to form a homopolymer, have a glass transition temperature equal to at least 50° C. Suitable alkoxy substituted alkyl methacrylates often have an alkyl group with 1 to 4 carbon atoms and an alkoxy group with 1 to 4 carbon atoms. An example is 2-methoxyethyl methacrylate. Suitable aryl methacrylates typically have an aryl group with 6 to 10 carbon atoms. An example aryl methacrylate is phenyl methacrylate. Suitable aralkyl methacrylates typically have aralkyl groups with 7 to 10 carbon atoms. An example aralkyl methacrylate is benzyl methacrylate. Suitable aryloxy-substituted alkyl methacrylates often have an aryloxy-substituted alkyl group with 7 to 10 carbon atoms. An example aryloxy-substituted alkyl methacrylate is 2-phenoxyethyl methacrylate. An example cyclic alkyl acrylate is cyclohexyl acrylate and an example bicyclic acrylate is isobornyl acrylate. Many of these monomers, when polymerized to form a homopolymer, have a glass transition temperature equal to at least 50° C.

In other embodiments, the first monomer composition used to form the A blocks and/or third monomer composition used to form the C block can include other optional monomers that are not (meth)acrylic-based monomers provided that greater than 50 weight percent of the monomers in the block are (meth)acrylic-based monomers and provided that the resulting polymeric blocks have a glass transition temperature that is equal to at least 50° C. when measured using Dynamic Mechanical Analysis. Examples of these other monomers are vinyl monomers such as styrene, styrene-type monomers (e.g., alpha-methyl styrene, 3-methyl styrene, 4-methyl styrene, ethyl styrene, isopropyl styrene, tert-butyl styrene, dimethyl styrene, 2,4,6-trimethyl styrene, and 4-methoxy styrene), vinyl acetate, and vinyl pyridine. Many of these monomers, when polymerized to form a homopolymer, have a glass transition temperature equal to at least 50° C.

In still other embodiments, the first monomer composition used to form the A blocks and/or third monomer composition used to form the C block can include various optional (meth)acrylic-based polar monomers provided the glass transition temperature of each resulting block is equal to at least 50° C. If present, these polar monomers are usually present in an amount no greater than 10 weight percent, no greater than 5 weight percent, no greater than 2 weight percent, or no greater than 1 weight percent based on a total weight of the monomers in the respective monomer composition. Suitable polar monomers include, for example, a (meth)acrylamide including N-alkyl (meth)acrylamides and N,N-dialkyl (meth)acrylamides, a (meth)acrylic acid, or a hydroxy-substituted alkyl (meth)acrylate. Specific polar monomers include, but are not limited to, (meth)acrylic acid, (meth)acrylamide, N-methyl (meth)acrylamide, N-ethyl (meth)acrylamide, N-isopropyl (meth)acrylamide, N,N-dimethyl (meth)acrylamide, N,N-diethyl (meth)acrylamide, 2-hydroxyethyl (meth)acrylate, and 2-hydroxypropyl (meth) acrylate. In many embodiments, however, there are no polar monomers in the A blocks and/or C block. The polar monomers may negatively impact the easy removability of the adhesive compositions and adhesive articles from a biological surface. Further, adhesive compositions formed without polar monomers may advantageously have fewer chemical interactions with biological surfaces such as skin.

Further, the composition of the A blocks of the (meth)acrylic-based triblock copolymer A-B-A can be the same as or different than the C block of the (meth)acrylic-based diblock copolymer C-D; they are selected to be the same in many embodiments. When the A blocks and the C block are the same (formed from identical monomeric compositions), compatibility of these blocks with each other can be maximized.

The A blocks of the (meth)acrylic-based triblock copolymer and/or the C block of the (meth)acrylic-based diblock copolymer are often a homopolymer formed from an alkyl methacrylate and the resulting polymeric block has a glass transition temperature equal to at least 50° C. as measured using Dynamic Mechanical Analysis. In some specific embodiments, the A blocks and the C block are the same homopolymer, which is a poly(alkyl methacrylate). In some more specific embodiments, the A blocks and/or the C block are poly(methyl methacrylate).

The B block of the (meth)acrylic-based triblock copolymer A-B-A and the D block of the (meth)acrylic-based diblock copolymer C-D are viscous polymeric blocks. As such, the B block and the D block are typically formed from monomers that will provide polymeric blocks having a glass transition temperature no greater than 20° C. as measured using Dynamic Mechanical Analysis. The B block and the D block typically are each prepared from a monomer composition that includes an alkyl acrylate. Stated differently, the B block is a polymeric material formed from a second monomer composition that includes an alkyl acrylate and the D block is a polymeric material formed from a fourth monomer composition that includes an alkyl acrylate. The alkyl acrylate used to form the D block can be the same or different than the alkyl acrylate used to form the B block. Suitable alkyl acrylates for forming the B block and the D block often have an alkyl group with 2 to 20 carbon atoms, 2 to 18 carbon atoms, 2 to 12 carbon atoms, or 2 to 10 carbon atoms. The alkyl group can be linear, branched, cyclic, or a combination thereof (e.g., the alkyl can have a cyclic group plus a branched or linear group).

Specific examples of alkyl acrylate monomers that can be used to form the B block and the D block include, but are not limited to, ethyl acrylate, n-propyl acrylate, n-butyl acrylate, isobutyl acrylate, sec-butyl acrylate, n-pentyl acrylate, isoamyl acrylate, n-hexyl acrylate, 2-methylbutyl acrylate, 4-methyl-2-pentyl acrylate, cyclohexyl acrylate, 2-methylhexyl acrylate, n-octyl acrylate, 2-octyl acrylate, isooctyl acrylate, 2-ethylhexyl acrylate, isononyl acrylate, n-decyl acrylate, isodecyl acrylate, lauryl acrylate, isotridecyl acrylate, isostearyl acrylate, and octadecyl acrylate. Many of these monomers, when polymerized to form a homopolymer, have a glass transition temperature no greater than 20° C. when measured using Dynamic Mechanical Analysis.

In some instances, the B block and the D block are homopolymers. The homopolymer B block can be the same or different than the homopolymer D block. Examples of homopolymers include, but are not limited to, poly(ethyl acrylate), poly(n-propyl acrylate), poly(n-butyl acrylate), poly(isobutyl acrylate), poly(sec-butyl acrylate), poly(isoamyl acrylate), poly(n-hexyl acrylate), poly(2-methylbutyl acrylate), poly(4-methyl-2-pentyl acrylate), poly(cyclohexyl acrylate), poly(2-methylhexyl acrylate), poly(n-octyl acrylate), poly(2-octyl acrylate), poly(isooctyl acrylate), poly(2-ethylhexyl acrylate), poly(isononyl acrylate), poly(n-decyl acrylate), poly(isodecyl acrylate), poly(lauryl acrylate), poly(isotridecyl acrylate), poly(isostearyl acrylate), and poly (octadecyl acrylate). In some more specific instances, the B block and the D block are poly(n-butyl acrylate), poly(n-octyl acrylate), poly(2-octyl acrylate), poly(isooctyl acrylate), poly(2-ethylhexyl acrylate), or poly(isononyl acrylate).

In addition to the alkyl acrylate monomers, the second monomer composition used to form the B block and the fourth monomer composition used to form the D block can include other optional monomers provided the resulting polymeric blocks have a glass transition temperature that is no greater than 20° C. when measured using Dynamic Mechanical Analysis.

In some embodiments, the second monomer composition used to form the B block and/or the fourth monomer composition used to form the D block can optionally include a heteroalkyl (meth)acrylate, an aralkyl acrylate, an aryloxy substituted alkyl acrylate, or an alkyl methacrylate having an alkyl group that is linear or branched with at least 6 carbon atoms. Suitable heteroalkyl acrylates include, but are not limited to 2-ethoxy ethyl (meth)acrylate, 2-methoxy ethyl acrylate, and 2-(2-ethoxyethoxy)ethyl acrylate. Suitable aralkyl acrylates include, but are not limited to, 2-biphenylhexyl acrylate and benzyl acrylate. An example aryloxy substituted alkyl acrylate is 2-phenoxy ethyl acrylate. Suitable alkyl methacrylates are n-decyl methacrylate, lauryl methacrylate, n-octyl methacrylate, isooctyl methacrylate, 2-ethylhexyl methacrylate, and n-hexyl methacrylate.

In still other embodiments, the second monomer composition used to form the B block and/or fourth monomer composition used to form the D block optionally can include various (meth)acrylic-based polar monomers provided the glass transition temperature of these blocks is no greater than 20° C. when measured using Dynamic Mechanical Analysis. If present, these polar monomers are usually present in an amount no greater than 10 weight percent, no greater than 5 weight percent, no greater than 2 weight percent, or no greater than 1 weight percent based on a total weight of the monomers in the respective monomer composition. Suitable polar monomers include, for example, a (meth)acrylamide including N-alkyl (meth)acrylamides and N,N-dialkyl (meth)acrylamides, a (meth)acrylic acid, or a hydroxy-substituted alkyl (meth)acrylate. Specific polar monomers include, but are not limited to, (meth)acrylic acid, (meth)acrylamide, N-methyl (meth)acrylamide, N-ethyl (meth)acrylamide, N-isopropyl (meth)acrylamide, N,N-dimethyl (meth)acrylamide, N,N-diethyl (meth)acrylamide, 2-hydroxyethyl (meth)acrylate, and 2-hydroxypropyl (meth)acrylate. In many embodiments, however, there are no polar monomers in the B block and/or D block. The polar monomers may negatively impact the easy removability of the adhesive compositions and adhesive articles from a biological surface. Further, adhesive compositions formed without polar monomers may advantageously have fewer chemical interactions with biological surfaces such as skin.

Further, the composition of the B block of the (meth)acrylic-based triblock copolymer A-B-A can be the same as or different than the D block of the (meth)acrylic-based diblock copolymer C-D; they are selected to be the same in many embodiments. When the B block and the D block are the same (formed from identical monomeric compositions), compatibility of these blocks with each other can be maximized.

The B block of the (meth)acrylic-based triblock copolymer and/or the D block of the (meth)acrylic-based diblock copolymer are often a homopolymer formed from an alkyl acrylate and the resulting polymeric block has a glass transition temperature no greater than 20° C. as measured using Dynamic Mechanical Analysis. In some specific embodiments, the B block and the D block are the same homopolymer, which is a poly(alkyl acrylate). In some more specific embodiments, the B blocks and/or the D block are poly(n-butyl acrylate), poly(n-octyl acrylate), poly(2-octyl acrylate), poly(isooctyl acrylate), poly(2-ethylhexyl acrylate), or poly(isononyl acrylate).

In many embodiments, the first monomer composition used to form the A blocks of the (meth)acrylic-based triblock copolymer A-B-A is the same as the third monomer composition used to form the C block of the (meth)acrylic-based diblock copolymer C-D and the second monomer composition used to form the B block of the (meth)acrylic-based triblock copolymer is the same as the fourth monomer composition used to form the D block of the (meth)acrylic-based diblock copolymer C-D.

In some embodiments, the A and C blocks are homopolymers, which are each a poly(alkyl methacrylate), and the B and D blocks are homopolymers, which are each a poly(alkyl acrylate). In some examples, the A blocks and the C block are prepared from the same alkyl methacrylate and the B and D blocks are prepared from the same alkyl acrylate. That is, the A blocks and the C block are the same poly(alkyl methacrylate) and the B block and the D block are the same poly(alkyl acrylate). The molecular weight (i.e., weight average molecular weight and/or number average molecular weight) of the A blocks may be the same as or different than that of the C block and the molecular weight of the B block may be the same as or different than that of the D block.

The optional (meth)acrylic-based triblock copolymer A-B-A can have a number average molecular weight ($M_n$) that is no less than 25 kiloDaltons (kDa), for example, no less than 30 kDa, no less than 35 kDa, no less than 40 kDa, no less than 45 kDa, or no less than 50 kDa. The (meth) acrylic-based triblock copolymer A-B-A can has a $M_n$ that is no greater than 150 kDa, for example, no greater than 140 kDa, no greater than 130 kDa, no greater than 120 kDa, no greater than 110 kDa, or no greater than 100 kDa. Thus, in some cases the $M_n$ of the (meth)acrylic-based triblock copolymer can be in a range of 25 kDa to 150 kDa, such as in a range of 30 kDa to 140 kDa, in a range of 35 kDa to 140 kDa, in a range of 35 kDa to 130 kDa, in a range of 40 kDa to 130 kDa, in a range of 40 kDa to 120 kDa, or in a range of 45 kDa to 120 kDa.

The polydispersity index (PDI) of the optional (meth) acrylic-based triblock copolymer A-B-A is typically 1.5 or less, such 1.3 or less, 1.2 or less, or 1.1 or less, although this is not required unless otherwise specified. Thus, the weight average molecular weight ($M_w$) of the (meth)acrylic-based triblock copolymer can be no less than 25 kDa, such as no less than 30 kDa, no less than 35 kDa, no less than 40 kDa, no less than 50 kDa, or no less than 55 kDa. The (meth) acrylic-based triblock copolymer can have an $M_w$ that is no greater than 160 kDa, for example, no greater than 150 kDa, no greater than 140 kDa, no greater than 130 kDa, no greater than 120 kDa, or no greater than 110 kDa. Exemplary $M_w$ of the (meth)acrylic-based triblock copolymer can be in a range of 25 kDa to 160 kDa, such as in a range of 30 kDa to 150 kDa, in a range of 35 kDa to 150 kDa, in a range of 40 kDa to 140 kDa, in a range of 40 kDa to 130 kDa, in a range of 40 kDa to 120 kDa, in a range of 50 kDa to 140 kDa, in a range of 50 kDa to 130 kDa, in a range of 50 kDa to 120 kDa, in a range of 55 kDa to 120 kDa, or in a range of 50 kDa to 110 kDa.

The (meth)acrylic-based diblock copolymer C-D typically has a number average molecular weight ($M_n$) that is no less than 25 kDa, no less than 35 kDa, no less than 40 kDa, no less than 45 kDa, or no less than 50 kDa. The $M_n$ of the (meth)acrylic-based diblock copolymer C-D is usually no greater than 100 kDa, no greater than 85 kDa, no greater than 80 kDa, no greater than 75 kDa, no greater than 70 kDa, no greater than 65 kDa, or no greater than 60 kDa. Exemplary ranges for the $M_n$ of the (meth)acrylic-based diblock copolymer include, but are not limited to, in a range of 25 kDa to 100 kDa, such as in a range of 25 kDa to 90 kDa, in a range of 25 kDa to 80 kDa, in a range of 25 kDa to 70 kDa, in a range of 25 kDa to 60 kDa, in a range of 35 kDa to 90 kDa, in a range of 35 kDa to 80 kDa, in a range of 30 kDa to 70 kDa, in a range of 35 kDa to 60 kDa, in a range of 40 kDa to 90 kDa, in a range of 40 kDa to 80 kDa, in a range of 40 kDa to 70 kDa, or in a range of 40 kDa to 60 kDa.

The polydispersity index of the (meth)acrylic-based diblock copolymer C-D is typically 1.5 or less, such 1.3 or less, 1.2 or less, or 1.1 or less, although this is not required unless otherwise specified. Thus, the weight average molecular weight ($M_w$) of the (meth)acrylic-based diblock is often no less than 30 kDa, no less than 35 kDa, or no less than 40 kDa. Similarly, the $M_w$ of the (meth)acrylic-based diblock is usually no more than 125 kDa, no more than 100 kDa, no more than 90 kDa, or no more than 80 kDa. Exemplary $M_w$ of the (meth)acrylic-based diblock can be in a range of 30 kDa to 125 kDa, in a range of 30 kDa to 100 kDa, in a range of 30 kDa to 90 kDa, in a range of 30 kDa to 80 kDa, in a range of 40 kDa to 125 kDa, in a range of 40 kDa to 100 kDa, or in a range of 40 kDa to 90 kDa. The weight average molecular weight and the number average molecular weight are typically determined using gel permeation chromatography with polystyrene standards.

The (meth)acrylic-based triblock copolymer and (meth) acrylic-based diblock copolymer can be synthesized using any suitable technique. Suitable techniques can include, for example, anionic polymerization, radical polymerization, group transfer polymerization, and ring-opening polymerization reactions. The polymerization can be a "living" or "controlled/living" polymerization, which can advantageously produce block copolymer structures that are well defined. Specific examples include atom transfer radical polymerization (ATRP) and reversible addition-fragmentation chain transfer polymerization (RAFT) processes.

Living polymerization techniques can lead to more stereo-regular block structures than blocks prepared using non-living or pseudo-living polymerization techniques, such as polymerization reactions that use iniferters. Stereo-regularity can be evidenced by highly syndiotactic or isotactic structures, and can result in well-controlled block structures. Such structures can influence the glass transition temperature of the block. For example, syndiotactic poly(methyl methacrylate) (PMMA) synthesized using living polymerization techniques can have a glass transition temperature that is as much as 20° C. to 25° C. higher than comparable atactic PMMA synthesized using non-living polymerization techniques. Thus, the glass transition temperature of the various blocks of the block copolymers can depend on the block copolymers stereo-regularity as well as on the monomer content of the block copolymers. Stereo-regularity can be detected, for example, using nuclear magnetic resonance spectroscopy. Structures with greater than about 75 percent stereo-regularity can often be obtained using living or controlled/living polymerization techniques, such as those discussed above. No particular degree stereo-regularity or tacticity is required for any of the blocks in the (meth) acrylic-based triblock copolymers or (meth)acrylic-based diblock copolymers, so long as the various blocks have the requisite glass transition temperatures.

Living polymerizations can also provide block copolymers with sharp transitions between the blocks. Block copolymers having a C block and a D block (and/or A blocks and a B block) can have regions on the border of the C block and the D block (and/or A blocks and the B block) that contain a mixture of monomeric units of C and monomer units of D (and/or monomeric units of A and monomeric units of B). When a living polymerization technique is used, the size of such regions can be minimized, or even eliminated, leading to a sharper transition from a C block to a D block (and/or from an A block to a B block), or from a D block to a C block (and/or from a B block to an A block). This can be beneficial when phase separation is desired, because a region of mixed monomeric units can be compatible with both blocks, thereby reducing the phase separation. On the other hand, a sharp transition with minimal regions of mixed monomeric units can promote phase separation.

When living polymerization techniques are used to form a block, the monomers can be contacted with an initiator in the presence of an inert diluent. The inert diluent can facilitate heat transfer and mixing of the initiator with the monomers. Typically, the inert diluent is one or more molecules that do not undergo a chemical reaction under the polymerization conditions. Although any suitable inert diluent can be used, saturated hydrocarbons, aromatic hydrocarbons, ethers, esters, ketones, and combinations thereof are often selected. Exemplary inert diluents include, but are not limited to, saturated aliphatic and cycloaliphatic hydrocarbons such as hexane, octane, cyclohexane, and the like; aromatic hydrocarbons such as benzene, toluene, and xylene; and aliphatic and cyclic ethers such as dimethyl ether, diethyl ether, tetrahydrofuran, and the like; esters such as ethyl acetate, butyl acetate, and the like; and ketones such as acetone, methyl ethyl ketone, methyl isobutyl ketone, and the like.

When block copolymers are prepared using living anionic polymerization techniques, the simplified structure A-M can represent a living A block where M is an initiator fragment that is typically selected from a Group I metal such as Li, Na, or K. The A block can be the polymerization product of a first monomer composition that includes an alkyl methacrylate. A second monomer composition that includes the monomers used to form the B block (e.g., an alkyl acrylate) can be added to A-M resulting in the formation of the living (meth)acrylic-based diblock structure A-B-M. The addition of another charge of the first monomer composition and the subsequent elimination of the living anion site, for example, by quenching, can result in the formation of triblock structure A-B-A. Alternatively, living (meth)acrylic-based diblock A-B-M structures can be coupled using difunctional or multifunctional coupling agents to form the (meth) acrylic-based triblock copolymers A-B-A.

Similarly, for formation of the (meth)acrylic-based diblock copolymer C-D, the C block can be the polymerization product of a third monomer composition that includes an alkyl methacrylate. A fourth monomer composition that includes the monomers (e.g., an alkyl acrylate) used to form the C block can be added to C-M resulting in the formation of the living (meth)acrylic-based diblock structure C-D-M.

Any initiator known in the art for living anionic polymerization reactions can be used. Typical initiators include alkali metal hydrocarbons such as organo-monolithium compounds, examples of which include ethyl lithium, n-propyl lithium, iso-propyl lithium, n-butyl lithium, sec-butyl lithium, tert-octyl lithium, n-decyl lithium, phenyl lithium, 2-naphthyl lithium, 4-butylphenyl lithium, 4-phenylbutyl lithium, cyclohexyl lithium, and the like. Such initiators can be referred to as monofunctional initiators because each molecule of initiator produces one anion. Monofunctional initiators can be useful in the preparation of a living block. For living anionic polymerization of (meth)acrylates, the reactivity of the anion can be tempered by the addition of one or more complexing ligands such as one or more of lithium chloride, crown ethers, or lithioethoxylates.

The initiator in living anionic polymerizations is often added drop wise to the monomers until a characteristic color that is typically associated with the anion of the initiator persists. The preliminary drop wise addition can destroy contaminants that react with initiator, thereby providing better control of the polymerization reaction. Then, the calculated amount of the initiator can be added to produce a polymer of the desired molecular weight. The amount of initiator needed for any particular molecular weight of polymer can be calculated by using a known amount of monomer and assuming that each molecule of initiator will produce a single polymer chain, all of which will be of equal length. This assumption is reasonably accurate for many living anionic polymerizations.

When the block copolymers are prepared using living free radical polymerization techniques, one or more free radical initiators can be used. Free radical initiators useful for living free radical polymerizations, as well as procedures for such polymerization, are known. For example, a detailed description can be found in International Patent Application Publication Nos. WO 97/18247 (Matyjaszewski et al.) and WO 98/01478 (Le et al.) as well as in the Handbook of Radical Polymerization (Matyjaszewski et al.).

The polymerization temperature used depends on the monomers being polymerized and on the type of polymerization technique used. In many cases, appropriate reaction temperatures for polymerization range from −100° C. to 200° C. For living anionic polymerization reactions, the appropriate temperature is often from −80° C. to 20° C. For living free radical polymerization reactions, the appropriate reaction temperature is often from 20° C. to 150° C.

The polymerization reaction can be carried out under controlled conditions so as to exclude substances that can destroy the initiator, living radical, or living anion. Typically, the polymerization reaction is carried out in an inert atmosphere such as nitrogen, argon, helium, or combinations thereof, although this is not required in all circumstances. When the reaction is a living anionic polymerization, anhydrous conditions can be used.

Some (meth)acrylic-based triblock copolymers A-B-A and (meth)acrylic-based diblock copolymers C-D are commercially available. For example, (meth)acrylic-based triblock copolymers are commercially available under the trade designation KURARITY from Kuraray America, Inc. (Houston, Tex., USA) and under the trade designation NANOSTRENGTH from Arkema (Tokyo, Japan). Example commercially available triblock copolymers include, but are not limited to, KURARITY LA2140, KURARITY LA2330, and KURARITY LA4285. Suitable (meth)acrylic-based diblock copolymers include, but are not limited to, KURARITY LA1114.

A (meth)acrylic-based composition is prepared that includes the (meth)acrylic-based diblock copolymer C-D and the optional (meth)acrylic-based triblock copolymer A-B-A. The (meth)acrylic-based composition typically contains 0 to less than 10 weight percent (meth)acrylic-based triblock copolymer A-B-A and greater than 90 to 100 weight percent (meth)acrylic-based diblock copolymer C-D. In most embodiments, the (meth)acrylic-based composition consists of the (meth)acrylic-based diblock copolymer C-D and the optional (meth)acrylic-based triblock copolymer A-B-A. That is, the (meth)acrylic-based composition is free of other (meth)acrylic-based polymers and/or (meth)acrylic-based copolymers. More specifically, the (meth)acrylic-based composition is typically free of other (meth)acrylic-based random copolymers or (meth)acrylic-based block copolymers other than the (meth)acrylic-based triblock A-B-A and the (meth)acrylic-based diblock C-D copolymers described herein. However, a small amount of remaining monomer could possibly be present in the (meth)acrylic-based composition. In some embodiments, at least 95 weight percent, at least 98 weight percent, at least 99 weight percent, or 100 weight percent of the (meth)acrylic-based composition comprises the optional (meth)acrylic-based triblock copolymer A-B-A and the (meth)acrylic-based diblock copolymer C-D.

Some example (meth)acrylic-based compositions contain 0 weight percent, at least 1 weight percent, at least 2 weight percent, at least 3 weight percent, at least 4 weight percent, or at least 5 weight percent (meth)acrylic-based triblock copolymer A-B-A. Such (meth)acrylic-based compositions can contain less than 10 weight percent, up to 9 weight percent, less than 9 weight percent, up to 8 weight percent, or up to 7 weight percent (meth)acrylic-based triblock copolymer. For example, the (meth)acrylic-based composition can contain 0 to less than 10 weight percent, 0 to 9 weight percent, 0 to less than 9 weight percent, 0 to 8 weight percent, 0 to 6 weight percent, 1 to less than 10 weight percent, 1 to 9 weight percent, 1 to less than 9 weight percent, 1 to 8 weight percent, 1 to 6 weight percent, 2 to less than 10 weight percent, 2 to 9 weight percent, 2 to less than 9 weight percent, 2 to 8 weight percent, or 2 to 6 weight percent (meth)acrylic-based triblock copolymer A-B-A. Each weight percent is based on the total weight of the (meth)acrylic-based composition. If the amount of the (meth)acrylic-based triblock copolymer is too high (such as 10 weight percent or more), the final adhesive composition that is crosslinked with electron-beam radiation and/or gamma ray radiation may have edge lift issues. For example, if the adhesive composition is adhered to a biological surface such as skin, the edges of the adhesive composition may lift away from the biological surface over time.

Some example (meth)acrylic-based compositions contain greater than 90 weight percent, at least 91 weight percent, greater than 91 weight percent, at least 92 weight percent, at least 94 weight percent, or at least 95 weight percent (meth)acrylic-based diblock copolymer C-D. Such (meth)acrylic-based compositions can contain 100 weight percent, up to 99 weight percent, up to 98 weight percent, up to 97 weight percent, up to 96 weight percent, or up to 95 weight percent (meth)acrylic-based diblock copolymer C-D. For example, the (meth)acrylic-based composition can contain greater than 90 to 100 weight percent, greater than 90 to 99 weight percent, greater than 90 to 98 weight percent, greater than 90 to 96 weight percent, greater than 90 to 95 weight percent, greater than 91 to 100 weight percent, greater than 91 to 99 weight percent, greater than 91 to 98 weight percent, greater than 91 to 96 weight percent, 92 to 100 weight percent, 92 to 99 weight percent, 92 to 98 weight percent, 92 to 96 weight percent, 94 to 100 weight percent, or 95 to 100 weight percent. Each weight percent is based on the total weight of the (meth)acrylic-based composition.

In some more specific examples, the (meth)acrylic-based composition contains 0 to less than 10 weight percent (meth)acrylic-based triblock copolymer A-B-A and greater than 90 to 100 weight percent (meth)acrylic-based diblock copolymer C-D, 1 to less than 10 weight percent (meth)acrylic-based triblock copolymer A-B-A and greater than 90 to 99 weight percent (meth)acrylic-based diblock copolymer C-D, 2 to less than 10 weight percent (meth)acrylic-based triblock copolymer A-B-A and greater than 90 to 98 weight percent (meth)acrylic-based diblock copolymer C-D, or 5 to less than 10 weight percent (meth)acrylic-based triblock copolymer A-B-A and greater than 90 to 95 weight percent (meth)acrylic-based diblock copolymer C-D. Each weight percent is based on the total weight of the (meth)acrylic-based composition.

In other examples, the (meth)acrylic-based composition contains 0 to less than 9 weight percent (meth)acrylic-based triblock copolymer A-B-A and greater than 91 to 100 weight percent (meth)acrylic-based diblock copolymer C-D, 1 to less than 9 weight percent (meth)acrylic-based triblock copolymer A-B-A and greater than 91 to 99 weight percent (meth)acrylic-based diblock copolymer C-D, 2 to less than 9 weight percent (meth)acrylic-based triblock copolymer A-B-A and greater than 91 to 98 weight percent (meth)acrylic-based diblock copolymer C-D, 5 to less than 9 weight percent (meth)acrylic-based triblock copolymer A-B-A and greater than 91 to 95 weight percent (meth)acrylic-based diblock copolymer C-D, 0 to 9 weight percent (meth)acrylic-based triblock copolymer A-B-A and 91 to 100 weight percent (meth)acrylic-based diblock copolymer C-D, 1 to 9 weight percent (meth)acrylic-based triblock copolymer A-B-A and 91 to 99 weight percent (meth)acrylic-based diblock copolymer C-D, 2 to 9 weight percent (meth)acrylic-based triblock copolymer A-B-A and 91 to 98 weight percent (meth)acrylic-based diblock copolymer C-D, or 5 to 9 weight percent (meth)acrylic-based triblock copolymer A-B-A and 91 to 95 weight percent (meth)acrylic-based diblock copolymer C-D. Each weight percent is based on the total weight of the (meth)acrylic-based composition.

In yet other examples, the (meth)acrylic-based composition contains 0 to 8 weight percent (meth)acrylic-based triblock copolymer A-B-A and 92 to 100 weight percent (meth)acrylic-based diblock copolymer C-D, 1 to 8 weight percent (meth)acrylic-based triblock copolymer A-B-A and greater than 92 to 99 weight percent (meth)acrylic-based diblock copolymer C-D, 2 to 8 weight percent (meth)acrylic-based triblock copolymer A-B-A and greater than 92 to 98 weight percent (meth)acrylic-based diblock copolymer C-D, or 5 to 8 weight percent (meth)acrylic-based triblock copolymer A-B-A and 92 to 95 weight percent (meth)acrylic-based diblock copolymer C-D. Each weight percent is based on the total weight of the (meth)acrylic-based composition.

The adhesive composition is exposed to electron beam radiation and/or gamma ray radiation to crosslink the (meth)acrylic-based composition. Any desired amount of radiation can be used depending on the particular use of the adhesive composition. For use next to a biological surface such as skin, the amount of radiation can be used to adjust the shear strength (e.g., cohesive strength) of the adhesive composition. Without any radiation, the shear strength may be undesirably low. If the shear strength is too low (the crosslinking is too low), the adhesive composition may not remove cleanly from the biological surface after its use. On the other hand, if the shear strength is too high (the crosslinking is too high), the adhesive composition may have edge lift issues when applied to a biological surface. In most cases, when the adhesive composition is used to secure an article to an adherent, the article can be readily removed by hand.

The adhesive composition is typically exposed to an amount of electron beam and/or gamma ray radiation sufficient to provide low or no adhesive residue when adhered to skin for 24 hours and then removed. Preferably, the adhesive composition leaves no adhesive residue on skin upon removal after 24 hours of contact with the skin. Although static shear strength can also be used to determine if the amount of radiation is sufficient, static shear strength can also be influenced by the amount of triblock copolymer and the amount of tackifier included in the adhesive composition. More particularly, static shear strength tends to increase with an increase in the amount of triblock included in the adhesive composition and tends to decrease with an increase in the amount of tackifier included in the adhesive composition.

For adhesive compositions that do not include a tackifier, the static shear is often in a range of 15 to 3000 minutes for a sheet of the adhesive composition having an area of 0.5 inches by 0.5 inches (1.3 centimeters by 1.3 centimeters) laminated to a stainless steel plate and connected to a 250 gram weight. The method of measuring the static shear strength is described more fully in the example section below. In some embodiments, the static shear strength is at least 20 minutes, at least 30 minutes, at least 40 minutes, at least 50 minutes, at least 60 minutes, at least 80 minutes, at least 100 minutes, at least 200 minutes, at least 300 minutes, at least 500 minutes, at least 750 minutes, or at least 1000 minutes. The static shear strength can be up to 3000 minutes, up to 2500 minutes, up to 2000 minutes, up to 1500 minutes, up to 1000 minutes, or up to 750 minutes. The static shear strength test results are influenced by the area laminated to the stainless steel plate. Thus, if the area of the sample in contact with the steel plate is increased, the static shear strength test results will be higher.

One of skill in the art can select the dosage of electron beam radiation and/or gamma ray radiation for a particular (meth)acrylic-based composition to get the desired properties such as shear strength and peel strength. When the (meth)acrylic-based composition does not include the optional (meth)acrylic-based triblock copolymer A-B-A, a relatively high dosage of radiation may be necessary to provide the desired shear strength. When the (meth)acrylic-based triblock copolymer A-B-A is present, however, a lower dosage of radiation may result in adhesive compositions with the desired shear strength because the triblock copolymer itself adds cohesive strength to the adhesive composition. Typically, the amount of radiation is in a range of 1 to 20 Mrads of electron beam radiation or 10 to 200 kilogray gamma ray radiation. For example, the dosage of electron beam radiation can be at least 1 Mrad, at least 2 Mrads, at least 4 Mrads, or at least 8 Mrads and can be up to 20 Mrads, up to 16 Mrads, or up to 12 Mrads. The dosage of gamma ray radiation can be at least 10 kilogray, at least 20 kilogray, at least 40 kilogray, at least 80 kilogray and can be up to 200 kilogray, up to 160 kilogray, or up to 120 kilogray.

In addition to providing the desired shear strength to the adhesive composition and the desired clean removability from biological surfaces through crosslinking of the adhesive composition, advantageously the electron beam radiation and/or gamma ray radiation can simultaneously provide sterilization of the adhesive composition. This can be particularly desirable for adhesive compositions that are applied to a biological surface such as skin.

The adhesive composition is typically free of chemical crosslinking agents. Chemical crosslinking agents may not be desirable when the adhesive composition is intended for application to biological surfaces such as skin. Many chemical crosslinking agents involve a reaction with various functional groups (such as acid groups, hydroxyl groups, or amino groups) that react with biological surfaces. In some embodiments, the adhesive compositions described herein do not have functional groups that can react with chemical crosslinking agents. For example, the (meth)acrylic-based diblock copolymer and optional (meth)acrylic-based triblock copolymers have pendant ester groups (more particularly, pendant alkyl ester groups) that typically do not react with biological surfaces such as skin.

In addition to being crosslinked by electron beam radiation and/or gamma ray radiation, the adhesive compositions is physically crosslinked because of the phase separated domains provided by the (meth)acrylic-based diblock copolymer C-D and the optional (meth)acrylic-based triblock copolymer A-B-A. The phase separated domains can have different morphologies depending on the relative amounts of the C and D blocks in the (meth)acrylic-based diblock copolymer and the relative amounts of the A and B blocks in the (meth)acrylic-based triblock copolymer, as well as the ratio of the (meth)acrylic-based diblock copolymer C-D to the (meth)acrylic-based triblock copolymer A-B-A. The multiphase morphology can give rise to physical crosslinking, whereby the C blocks of the (meth)acrylic-based diblock copolymer associate with the A blocks of the (meth)acrylic-based triblock copolymer and the D blocks of the (meth)acrylic-based diblock copolymer associate with the B blocks of the (meth)acrylic-based triblock copolymer. This physical crosslinking is different than chemical crosslinking in that physical crosslinking forms crosslinks by non-covalent interactions rather than by the formation of covalent chemical bonds. The extent or strength of the physical crosslinking can be maximized by selecting A blocks of the (meth)acrylic-based triblock copolymer A-B-A that are highly compatible with each other as well as with the C block of the (meth)acrylic-based diblock copolymer. Thus, the A blocks of the (meth)acrylic-based triblock copolymer A-B-A are often selected to have the same chemical identity and are also often selected to have the same chemical identity as the C block of the (meth)acrylic-based diblock copolymer C-D. Further, the D block of the (meth)acrylic-based diblock copolymer C-D and the B block of the (meth)acrylic (meth)acrylic-based triblock copolymer A-B-A are often selected to have the same chemical identity.

In addition to the chemical identity of the various blocks of the (meth)acrylic-based triblock copolymer and the (meth)acrylic-based diblock copolymer, the extent of physical crosslinking and ultimate properties of the adhesive composition can also depend on the relative weights of the A and B blocks of the (meth)acrylic-based triblock copolymer and the relative weight of the C and D blocks of the (meth)acrylic-based diblock copolymer. The nanodomains of the hard A and C blocks can be responsible for physical crosslinking of the adhesive composition. Higher amounts of physical crosslinking can relate to increased shear strength of the adhesive composition. As such, increasing the A block content of the (meth)acrylic-based triblock copolymer and/or increasing the C block content of the (meth)acrylic-based diblock copolymer tends to increase the cohesive strength of the adhesive composition.

The matrix formed by the B block of the (meth)acrylic-based triblock copolymer A-B-A and the D block of the (meth)acrylic-based diblock copolymer C-D in the adhesive composition can be responsible for the tackiness of the adhesive compositions. Accordingly, an adhesive composition having a lower B block content (or conversely, a higher A block content) of the (meth)acrylic-based triblock copolymer and/or having a lower D block content (or conversely, a higher C block content) of the (meth)acrylic-based diblock copolymer may not have sufficient tackiness to readily adhere to a surface of interest such as skin.

In addition to the (meth)acrylic-based composition, the adhesive composition can further comprise one or more additives such as, for example, at least one plasticizer, at least one tackifier, at least one filler, or a combination thereof.

Plasticizers can include phthalate esters, adipate esters, phosphate esters, citrate esters, sugar derivatives, poly(ethylene glycol), and poly(ethylene glycol) functionalized organic molecules. Exemplary plasticizers include, but are not limited to, one or more of phthalate ester, bis(2-ethylhexyl)adipate, dimethyl adipate, monomethyl adipate, dioxtyl adipate, dibutyl sebacate, dibutyl maleate, biisobutyl maleate, benzoates, terephthalates, 1,2-cyclohexane dicarboxylic acid diisononyl ester, epoxidized vegetable oil, alkyl sulphonic acid phenyl ester, N-ethyl toluene sulfonamide, N-(2-hydroxypropyl)benzene sulfonamide, N-(n-butyl benzene sulfonamide, sucrose acetate isobutyrate, tricresyl phosphate, tributyl phosphate, triethylene glycol dihexanoate, tetraethylene glycol diheptanoate, triethyl citrate, acetyl triethyl citrate, tributyl citrate, acetyl tributyl citrate, trioctyl citrate, acetyl trioctyl citrate, trihexyl citrate, acetyl trihexyl citrate, butyryl trihexyl citrate, trimethyl citrate, sucrose acetate isobutyrate, and acetylated monoglyceride.

Tackifiers can include rosins, hydrocarbon resins, terpenes, and MQ silicate resins. Exemplary tackifiers can include one or more of rosin (which can be at least partially hydrogenated), rosin derivative (which can be at least partially hydrogenated), terpenes, modified terpenes, C5 aliphatic resins, C9 aromatic resins, C5/C9 aliphatic/aromatic resins, hydrogenated hydrocarbon resin, terpene-phenol resin, poly(alpha-methylstyrene) (AMS) resin, poly(styrene) resins (also known as Pure Monomer Resins), copolymers of (alpha-methylstyrene) and styrene resins, and phenolic modified AMS resins, and MQ silicate resin. Some suitable tackifiers are obtainable under the trade designation KRISTALEX 1120, 3100, 5140 and PLASTOLYN 240, 290 (Eastman Chemical Company, Kingsport, Tenn., USA), YS RESIN SX 100 (Yasuhara Chemical Co., Ltd., Hiroshima, Japan), NORSOLENE W-100 (Cray Valley Division of Total Petrochemicals and Refining, Inc., Houston, Tex., USA), SYLVARES 520, 525, 540, SA85, SA100, SA120, SA140, TP115P (Arizona Chemical Inc., Jacksonville, Fla., USA), and PICCOPLASTIC A5 Hydrocarbon Resin (Eastman Chemical Company, Kingsport, Tenn., USA).

Fillers can include any appropriate inert inorganic particle. Exemplary fillers include one or more of alumina trihydrate, talc, ceramic, rock, coal, ground glass, glass beads, particulate plastics, non-catalytic metals, sand, silica, calcium carbonate, and magnesium carbonate.

The total amount of plasticizer, tackifier, and filler, if any, are often included in the composition in an amount up to 45 weight percent based on a total weight of the (meth)acrylic-based composition in the adhesive composition. In some embodiments, the total amount of these additives can be up to 40 weight percent, up to 35 weight percent, up to 30 weight percent, up to 25 weight percent, or up to 20 weight percent based on the total weight of the (meth)acrylic-based composition. The total amount of these additives, if present, is often at least 0.1 weight percent, at least 0.5 weight percent, at least 1 weight percent, at least 2 weight percent, at least 5 weight percent, at least 10 weight percent, or at least 15 weight percent based on the total weight of the (meth)acrylic-based composition.

That is, the adhesive composition can include a) a (meth)acrylic-based composition containing greater than 90 to 100 weight percent (meth)acrylic-based diblock copolymer C-D, 0 to less than 10 weight percent (meth)acrylic-based triblock copolymer A-B-A, and b) 0 to 45 weight percent additives (plasticizer, tackifier, and filler) based on a total weight of the (meth)acrylic-based composition. This is equivalent to saying that the adhesive composition contains a) 100 parts by weight of the (meth)acrylic-based composition and b) 0 to 45 parts by weight additives per 100 parts by weight of (meth)acrylic-based composition. The 100 parts by weight of the (meth)acrylic-based composition contains 0 to less than 10 parts by weight (meth)acrylic-based triblock copolymer A-B-A and greater than 90 to 100 parts by weight (meth)acrylic-based diblock copolymer.

Stated differently, the adhesive composition contains about 70 to 100 weight percent (meth)acrylic-based composition and 0 to 30 weight percent additives. More particularly, considering the portion of the (meth)acrylic-based diblock copolymer and of the (meth)acrylic-based triblock copolymer, the adhesive composition comprises 0 to less than 7 weight percent (meth)acrylic-based triblock copolymer A-B-A, greater than 93 to 100 weight percent (meth)acrylic-based diblock copolymer C-D, and 0 to 45 weight percent additives. These percent weight values are based on a total weight of the adhesive composition.

In some embodiments, the adhesive composition contains 75 to 100 weight percent (meth)acrylic-based composition and 0 to 25 weight percent additives, 75 to 95 weight percent (meth)acrylic-based composition and 5 to 25 weight percent additives, 80 to 100 weight percent (meth)acrylic-based composition and 0 to 20 weight percent additives, 80 to 95 weight percent (meth)acrylic-based composition and 5 to 20 weight percent additives, 80 to 100 weight percent (meth)acrylic-based composition and 0 to 20 weight percent additives, 80 to 95 weight percent (meth)acrylic-based composition and 5 to 20 weight percent additives, or 95 to 100 weight percent (meth)acrylic-based composition and 0 to 5 weight percent additives.

In another aspect, an adhesive article is provided. The article includes a substrate and an adhesive composition layer positioned adjacent to the substrate. That is, the adhesive composition layer has a first major surface attached to the substrate. The adhesive composition layer can be attached directly or indirectly to the substrate. For example, the substrate and the adhesive composition layer can be separated by a primer layer or an adhesion promoting layer, if desired.

The substrate included in the adhesive article can be any suitable substrate such as, for example, a polymeric material, glass, ceramic material, or metal. In many embodiments, the substrate is a polymeric material such as, for example, a polymeric sheet or a fabric substrate, such as a woven fabric substrate or a non-woven fabric substrate. Typical polymeric substrates are often prepared from polyurethane, polyethylene, polypropylene, polyester such as poly(ethylene terephthalate or polylactic acid), cellulosic material, polyamide, or the like. The substrate can be rigid or flexible, colored or clear, and of any desired size and shape. In many embodiments, the substrate is a backing layer for the adhesive article and provides a non-tacky surface. That is, the adhesive article has an adhesive composition layer with a first tacky surface (resulting from the adhesive composition layer) that can be adhered to any desired surface and a second non-tacky outer surface that is opposite the first tacky surface (resulting from the substrate).

The adhesive articles can be used for any desired purpose. In some embodiments, a second major surface of the adhesive composition layer (which is opposite the first major surface positioned adjacent to the substrate) is adhered to a biological surface such as skin. As such, the adhesive article can be used, for example, in medical, veterinary, pharmaceutical, or surgical procedures. For example, an adhesive article can be placed over a wound to treat a wound. The adhesive article can also be placed over a catheter, intravenous needle, or inter-arterial needle that is at least partially inserted into a subject, for example, into a lumen of a subject, in order to stabilize the catheter, intravenous needle, or inter-arterial needle. The adhesive article can also be used to secure a medical device to a subject.

When the adhesive article is applied to a biological surface, it can be desirable to include a pharmaceutically active agent (i.e., pharmaceutical agent). Suitable pharmaceutically active agents are those that are typically applied topically to a biological surface. Exemplary topically administrable pharmaceutically active agents include anti-microbials, anti-fungals, anti-inflammatory agents, including but not limited to steroidal anti-inflammatory agents and non-steroidal anti-inflammatory drugs (NSAIDs), vitamins, beneficial oils, moisturizers, and the like. Specific topically administrable pharmaceutically active agents include iodine, povidone-iodine, silver, salicylic acid or salts thereof, acetylsalicylic acid or salts thereof, chlorhexidine, such as chlorhexidine gluconate, sulfacetamide and salts thereof, erythromycin, neomycin, polymyxin, bacitracin, retapamulin, mupirocin, gentamicin, mefenide, lidocaine, tetracycline, benzoic acid, ciclopirox olamine, undecylenic alkanolamide, bifonazole, clotramazoel, econazole, ketoconazole, miconazole, tioconazole, terbinafine, tolciclate, tolnaftate, tymol, sulfacetamide, almond oil, argan oil, avocado oil, camelina oil, coconut oil, jojoba oil, rose oil, sesame seed oil, shea oil, hemp seed oil, macadamia nut oil, lanolin, vitamins such as vitamin A, vitamin A palmitate, vitamin B3, vitamin C, and tocopherols and esters thereof, such as alpha-tocopherol and alpha-tocopheryl acetate. Such pharmaceutically active agents can be used in any suitable amount, such as up to 20 weight percent, up to 15 weight percent, up to 10 weight percent, up to 5 weight percent, up to 2 weight percent, or up to 1 weight percent based on the total weight of the adhesive composition layer. In many embodiments, the pharmaceutical agent is present as a layer on an outer surface of the adhesive composition layer opposite the substrate.

In other applications, an additional layer can be positioned between the adhesive composition layer and the biological surface, such as skin, to function as an absorbent. An absorbent layer is particularly advantageous if the adhesive article is used as a wound dressing. The adsorbent layer is often a foam, gauze, hydrocolloid, or any other suitable wound control layer. These layers are often positioned such that part of the adhesive composition layer (e.g., the outer edge of the adhesive composition layer) is still in contact with the biological surface.

Adhesive articles comprising the adhesive composition described herein can provide low or minimal edge lift over an applicable period of time. An applicable period of time can be, for example, up to two weeks, up to twelve days, up to ten days, up to one week, up to five days, up to three days, or up to two days. An applicable period of time can also be at least one day, at least two days, at least three days, at least five days, or at least one week. Low or minimal edge lift is particularly useful when the adhesive article is used, for example, as a wound dressing, to stabilize a catheter, to affix and intravenous or inter-arterial needle, or to affix a medical device.

The adhesive compositions and articles can have excellent adhesion to biological surfaces such as skin over a sufficient period of time while being removable without leaving an unacceptable amount of residue on the skin. Also, the resulting adhesive compositions can have low static shear strength when measured on stainless steel. That an adhesive composition can have this combination of properties is surprising, because low shear strength is typically associated with adhesives that have low cohesive strength, whereas a low amount of residuals is typically associated with adhesives that have high cohesive strength. Removal of the adhesive compositions and articles can usually occur without painfully pulling on the skin to which the adhesive composition has been adhered.

The adhesive compositions can be adhered to the skin without significant edge lift for a period of one day to 2 weeks or more. Depending on the application, this period of time can be one day or more, two days or more, three days or more, four days or more, five days or more, six days or more, or seven days or more. For some applications, the period of time is two weeks or less, thirteen days or less, twelve days or less, eleven days or less, ten days or less, nine days or less, or seven days or less. For some applications, the period of time is one week.

The adhesive compositions and adhesive articles containing the adhesive compositions usually have sufficient tackiness to adhere quickly to biological surfaces, can be removed easily from skin (i.e., can be removed without pulling excessively (painfully) on the skin), can be removed cleanly from skin (i.e., can be removed leaving little or no residue), and can adhere to skin with minimal or no edge lift (i.e., the edges of the adhesive article typically remain in contact with the skin during use).

In another aspect, a method of making an adhesive article is provided. The method includes providing an adhesive composition (i.e., any of the adhesive compositions described above). The method further includes forming an adhesive composition layer adjacent (e.g., adhered directly or indirectly) to a substrate. Any of the substrates described above can be used. The adhesive composition can be in direct contact with the substrate or can be separated from the substrate by one of more layers such as a primer layer or adhesion promoter layer. The method still further includes exposing the adhesive composition layer to electron beam radiation and/or gamma ray radiation to crosslink the adhesive composition layer.

Various embodiments are provided that include an adhesive composition, an adhesive article that includes the adhesive composition, and a method of making the adhesive articles.

Embodiment 1A is an adhesive composition that contains a crosslinked polymeric product of (a) a reaction mixture containing a (meth)acrylic-based composition and (b) electron beam radiation and/or gamma ray radiation. The (meth)acrylic-based composition contains (1) 0 to less than 10 weight percent of a (meth)acrylic-based triblock copolymer A-B-A and (2) greater than 90 to 100 weight percent of a (meth)acrylic-based diblock copolymer C-D. The weight percent amounts are based on a total weight of the (meth) acrylic-based composition. The optional (meth)acrylic-based triblock copolymer A-B-A contains 20 to 55 weight percent A blocks and 45 to 80 weight percent B block based on a total weight of the triblock copolymer A-B-A. Each A block is a polymerized product of a first monomer composition comprising an alkyl methacrylate and the B block is a polymerized product of a second monomer composition comprising an alkyl acrylate. The (meth)acrylic-based diblock copolymer C-D contains 5 to 30 weight percent C blocks and 70 to 95 weight percent D block based on a total weight of the (meth)acrylic-based diblock copolymer C-D. The C block a polymerized product of a third monomer composition comprising an alkyl methacrylate and the D block is a polymerized product of a fourth monomer composition comprising an alkyl acrylate.

Embodiment 2A is the adhesive composition of embodiment 1A, wherein the (meth)acrylic-based composition is 100 weight percent (meth)acrylic-based diblock copolymer C-D.

Embodiment 3A is the adhesive composition of embodiment 1A or 2A, wherein the (meth)acrylic-based composition is 0 to less than 10 weight percent (meth)acrylic-based triblock copolymer A-B-A and b) greater than 90 to 100 weight percent of a (meth)acrylic-based diblock copolymer C-D.

Embodiment 4A is the adhesive composition of any one of embodiments 1A to 3A, wherein the (meth)acrylic-based composition is 1 to less than 10 weight percent (meth)acrylic-based triblock copolymer A-B-A and b) greater than 90 to 99 weight percent of a (meth)acrylic-based diblock copolymer C-D.

Embodiment 5A is the adhesive composition of any one of embodiments 1A to 4A, wherein the (meth)acrylic-based composition is 0 to less than 9 weight percent (meth)acrylic-based triblock copolymer A-B-A and b) greater than 91 to 100 weight percent of a (meth)acrylic-based diblock copolymer C-D.

Embodiment 6A is the adhesive composition of any one of embodiments 1A to 5A, wherein the (meth)acrylic-based composition is 1 to less than 9 weight percent (meth)acrylic-based triblock copolymer A-B-A and b) greater than 91 to 99 weight percent of a (meth)acrylic-based diblock copolymer C-D.

Embodiment 7A is the adhesive composition of any one of embodiments 1A to 6A, wherein the (meth)acrylic-based composition is 0 to 9 weight percent (meth)acrylic-based triblock copolymer A-B-A and b) 91 to 100 weight percent of a (meth)acrylic-based diblock copolymer C-D.

Embodiment 8A is the adhesive composition of any one of embodiments 1A to 7A, wherein the (meth)acrylic-based composition is 1 to 9 weight percent (meth)acrylic-based triblock copolymer A-B-A and b) 91 to 99 weight percent of a (meth)acrylic-based diblock copolymer C-D.

Embodiment 9A is the adhesive composition of any one of embodiments 1A to 8A, wherein the (meth)acrylic-based composition is 0 to 8 weight percent (meth)acrylic-based triblock copolymer A-B-A and b) 92 to 100 weight percent of a (meth)acrylic-based diblock copolymer C-D.

Embodiment 10A is the adhesive composition of any one of embodiments 1A to 9A, wherein the (meth)acrylic-based composition is 1 to 8 weight percent (meth)acrylic-based triblock copolymer A-B-A and b) 92 to 99 weight percent of a (meth)acrylic-based diblock copolymer C-D.

Embodiment 11A is the adhesive composition of any one of embodiments 1A to 10A, wherein the A blocks have a glass transition temperature equal to at least 50° C. when measured using Dynamic Mechanical Analysis and wherein the B block has a glass transition temperature no greater than 20° C.

Embodiment 12A is the adhesive composition of any one of embodiments 1A to 10A, further comprising an additive selected from a tackifier, plasticizer, filler, or combination thereof.

Embodiment 13A is the adhesive composition of any one of embodiments 1A to 12A, wherein the adhesive composition comprises 70 to 100 weight percent of the (meth)acrylic-based composition and 0 to 30 weight percent of an additive selected from a tackifier, plasticizer, filler, or combination thereof.

Embodiment 14A is the adhesive composition of any one of embodiments 1A to 13A, wherein at least 95 weight percent, at least 98 weight percent, at least 99 weight percent, or 100 weight percent of the (meth)acrylic-based composition comprises the (meth)acrylic-based triblock copolymer A-B-A and the (meth)acrylic-based diblock copolymer C-D.

Embodiment 15A is the adhesive composition of any one of embodiments 1A to 14A, wherein the A blocks of the (meth)acrylic-based triblock copolymer A-B-A and the C block of the (meth)acrylic-based diblock copolymer C-D comprise the same alkyl methacrylate having a glass transition temperature as a homopolymer that is at least 50° C. when measured using Dynamic Mechanical Analysis.

Embodiment 16A is the adhesive composition of any one of embodiments 1A to 15A, wherein the A blocks of the (meth)acrylic-based triblock copolymer A-B-A and the C block of the (meth)acrylic-based diblock copolymer C-D comprise the same alkyl methacrylate having a glass transition temperature as a homopolymer that is at least 70° C. when measured using Dynamic Mechanical Analysis.

Embodiment 17A is the adhesive composition of any one of embodiments 1A to 16A, wherein the B block of the (meth)acrylic-based triblock copolymer A-B-A and the D block of the (meth)acrylic-based diblock copolymer comprise the same alkyl acrylate having a glass transition temperature as a homopolymer that is no greater than 20° C. when measured using Dynamic Mechanical Analysis.

Embodiment 18A is the adhesive composition of any one of embodiments 1A to 17A, wherein the B block of the (meth)acrylic-based triblock copolymer A-B-A and the D block of the (meth)acrylic-based diblock copolymer comprise the same alkyl acrylate having a glass transition temperature as a homopolymer that is no greater than 0° C. when measured using Dynamic Mechanical Analysis.

Embodiment 19A is the adhesive composition of any one of embodiments 1A to 18A, wherein the A blocks of the (meth)acrylic-based triblock copolymer A-B-A are formed from a first monomer composition and the C block of the (meth)acrylic-based diblock copolymer C-D is formed from a third monomer composition and wherein the first monomer composition is identical to the third monomer composition.

Embodiment 20A is the adhesive composition of any one of embodiments 1A to 19A, wherein the B block of the (meth)acrylic-based triblock copolymer A-B-A is formed from a second monomer composition and the D block of the (meth)acrylic-based diblock copolymer C-D is formed from a fourth monomer composition and wherein the second monomer composition is identical to the fourth monomer composition.

Embodiment 21A is the adhesive composition of any one of embodiments 1A to 20A, wherein the A blocks of the (meth)acrylic-based triblock copolymer A-B-A and the C block of the C-D (meth)acrylic-based diblock copolymer are poly(methyl methacrylate).

Embodiment 22A is the adhesive composition of any one of embodiments 1A to 21A, wherein the B block of the (meth)acrylic-based triblock copolymer A-B-A and the D block of the C-D (meth)acrylic-based diblock copolymer are each poly(n-butyl acrylate), poly(isooctyl acrylate), poly(2-octyl acrylate), poly(isobornyl acrylate), or poly(2-ethylhexyl acrylate).

Embodiment 23A is the adhesive composition of any one of embodiments 1A to 22A, wherein there is no (meth)acrylic-based triblock copolymer A-B-A, the C block of the C-D (meth)acrylic-based diblock is poly(methyl methacrylate), and the D block of the C-D (meth)acrylic-based diblock copolymer is poly(n-butyl acrylate), poly(isooctyl acrylate), poly(2-octyl acrylate), poly(isobornyl acrylate), or poly(2-ethylhexyl acrylate).

Embodiment 24A is the adhesive composition of any one of embodiments 1A to 23A, wherein the (meth)acrylic-based triblock copolymer A-B-A has a number average molecular weight ($M_n$) in a range of 25 to 150 kDaltons.

Embodiments 25A is the adhesive composition of any one of embodiments 1A to 24A, wherein the (meth)acrylic-based diblock copolymer C-D has a number average molecular weight ($M_n$) in a range of 25 to 100 kDaltons.

Embodiment 26A is the adhesive composition of any one of embodiments 1A to 25A, wherein the adhesive composition leaves no adhesive residue upon removal after being adhered to skin for 24 hours.

Embodiment 27A is the adhesive composition of any one of embodiments 1A to 26A, wherein the electron beam radiation is in a range of 1 to 20 Mrads and/or the gamma ray radiation is in a range of 10 to 200 kilograys.

Embodiment 1B is an adhesive article that includes a substrate and an adhesive composition layer having a first major surface attached to the substrate. The adhesive composition layer contains a crosslinked polymeric product of (a) a reaction mixture containing a (meth)acrylic-based composition and (b) electron beam radiation and/or gamma ray radiation. The (meth)acrylic-based composition includes (1) 0 to less than 10 weight percent of a (meth)acrylic-based triblock copolymer A-B-A and (2) greater than 90 to 100 weight percent of a (meth)acrylic-based diblock copolymer C-D. The weight percent amounts are based on a total weight of the (meth)acrylic-based composition. The optional (meth) acrylic-based triblock copolymer A-B-A contains 20 to 55 weight percent A blocks and 45 to 80 weight percent B block based on a total weight of the triblock copolymer A-B-A. Each A block is a polymerized product of a first monomer composition comprising an alkyl methacrylate and the B block is a polymerized product of a second monomer composition comprising an alkyl acrylate. The (meth) acrylic-based diblock copolymer C-D contains 5 to 30 weight percent C block and 70 to 95 weight percent D block based on a total weight of the (meth)acrylic-based diblock copolymer C-D. The C block is a polymerized product of a third monomer composition comprising an alkyl methacrylate and the D block is a polymerized product of a fourth monomer composition comprising an alkyl acrylate.

Embodiment 2B is the adhesive article of embodiment 1B, wherein the (meth)acrylic-based composition is 100 weight percent (meth)acrylic-based diblock copolymer C-D.

Embodiment 3B is the adhesive article of embodiment 1B or 2B, wherein the (meth)acrylic-based composition is 0 to less than 10 weight percent (meth)acrylic-based triblock copolymer A-B-A and b) greater than 90 to 100 weight percent of a (meth)acrylic-based diblock copolymer C-D.

Embodiment 4B is the adhesive article of any one of embodiments 1B to 3B, wherein the (meth)acrylic-based composition is 1 to less than 10 weight percent (meth) acrylic-based triblock copolymer A-B-A and b) greater than 90 to 99 weight percent of a (meth)acrylic-based diblock copolymer C-D.

Embodiment 5B is the adhesive article of any one of embodiments 1B to 4B, wherein the (meth)acrylic-based composition is 0 to less than 9 weight percent (meth)acrylic-based triblock copolymer A-B-A and b) greater than 91 to 100 weight percent of a (meth)acrylic-based diblock copolymer C-D.

Embodiment 6B is the adhesive article of any one of embodiments 1B to 5B, wherein the (meth)acrylic-based composition is 1 to less than 9 weight percent (meth)acrylic-based triblock copolymer A-B-A and b) greater than 91 to 99 weight percent of a (meth)acrylic-based diblock copolymer C-D.

Embodiment 7B is the adhesive article of any one of embodiments 1B to 6B, wherein the (meth)acrylic-based composition is 0 to 9 weight percent (meth)acrylic-based triblock copolymer A-B-A and b) 91 to 100 weight percent of a (meth)acrylic-based diblock copolymer C-D.

Embodiment 8B is the adhesive article of any one of embodiments 1B to 7B, wherein the (meth)acrylic-based composition is 1 to 9 weight percent (meth)acrylic-based triblock copolymer A-B-A and b) 91 to 99 weight percent of a (meth)acrylic-based diblock copolymer C-D.

Embodiment 9B is the adhesive article of any one of embodiments 1B to 8B, wherein the (meth)acrylic-based composition is 0 to 8 weight percent (meth)acrylic-based triblock copolymer A-B-A and b) 92 to 100 weight percent of a (meth)acrylic-based diblock copolymer C-D.

Embodiment 10B is the adhesive article of any one of embodiments 1B to 9B, wherein the (meth)acrylic-based composition is 1 to 8 weight percent (meth)acrylic-based triblock copolymer A-B-A and b) 92 to 99 weight percent of a (meth)acrylic-based diblock copolymer C-D.

Embodiment 11B is the adhesive article of any one of embodiments 1B to 10B, wherein the A blocks have a glass transition temperature equal to at least 50° C. when measured using Dynamic Mechanical Analysis and wherein the B block has a glass transition temperature no greater than 20° C.

Embodiment 12B is the adhesive article of any one of embodiments 1B to 10B, further comprising an additive selected from a tackifier, plasticizer, filler, or combination thereof.

Embodiment 13B is the adhesive article of any one of embodiments 1B to 12B, wherein the adhesive composition comprises 70 to 100 weight percent of the (meth)acrylic-based composition and 0 to 30 weight percent of an additive selected from a tackifier, plasticizer, filler, or combination thereof.

Embodiment 14B is the adhesive article of any one of embodiments 1B to 13B, wherein at least 95 weight percent, at least 98 weight percent, at least 99 weight percent, or 100 weight percent of the (meth)acrylic-based composition comprises the (meth)acrylic-based triblock copolymer A-B-A and the (meth)acrylic-based diblock copolymer C-D.

Embodiment 15B is the adhesive article of any one of embodiments 1B to 14B, wherein the A blocks of the (meth)acrylic-based triblock copolymer A-B-A and the C block of the (meth)acrylic-based diblock copolymer C-D comprise the same alkyl methacrylate having a glass transition temperature as a homopolymer that is at least 50° C. when measured using Dynamic Mechanical Analysis.

Embodiment 16B is the adhesive article of any one of embodiments 1B to 15B, wherein the A blocks of the (meth)acrylic-based triblock copolymer A-B-A and the C block of the (meth)acrylic-based diblock copolymer C-D comprise the same alkyl methacrylate having a glass transition temperature as a homopolymer that is at least 70° C. when measured using Dynamic Mechanical Analysis.

Embodiment 17B is the adhesive article of any one of embodiments 1B to 16B, wherein the B block of the (meth)acrylic-based triblock copolymer A-B-A and the D block of the (meth)acrylic-based diblock copolymer comprise the same alkyl acrylate having a glass transition temperature as a homopolymer that is no greater than 20° C. when measured using Dynamic Mechanical Analysis.

Embodiment 18B is the adhesive article of any one of embodiments 1B to 17B, wherein the B block of the (meth)acrylic-based triblock copolymer A-B-A and the D block of the (meth)acrylic-based diblock copolymer comprise the same alkyl acrylate having a glass transition temperature as a homopolymer that is no greater than 0° C. when measured using Dynamic Mechanical Analysis.

Embodiment 19B is the adhesive article of any one of embodiments 1B to 18B, wherein the A blocks of the (meth)acrylic-based triblock copolymer A-B-A are formed from a first monomer composition and the C block of the (meth)acrylic-based diblock copolymer C-D is formed from a third monomer composition and wherein the first monomer composition is identical to the third monomer composition.

Embodiment 20B is the adhesive article of any one of embodiments 1B to 19B, wherein the B block of the (meth)acrylic-based triblock copolymer A-B-A is formed from a second monomer composition and the D block of the (meth)acrylic-based diblock copolymer C-D is formed from a fourth monomer composition and wherein the second monomer composition is identical to the fourth monomer composition.

Embodiment 21B is the adhesive article of any one of embodiments 1B to 20B, wherein the A blocks of the (meth)acrylic-based triblock copolymer A-B-A and the C block of the C-D (meth)acrylic-based diblock copolymer are poly(methyl methacrylate).

Embodiment 22B is the adhesive article of any one of embodiments 1B to 21B, wherein the B block of the (meth)acrylic-based triblock copolymer A-B-A and the D block of the C-D (meth)acrylic-based diblock copolymer are each poly(n-butyl acrylate), poly(isooctyl acrylate), poly(2-octyl acrylate), poly(isobornyl acrylate), or poly(2-ethylhexyl acrylate).

Embodiment 23B is the adhesive article of any one of embodiments 1B to 22B, wherein there is no (meth)acrylic-based triblock copolymer A-B-A, the C block of the C-D (meth)acrylic-based diblock is poly(methyl methacrylate) and the D block of the C-D (meth)acrylic-based diblock copolymer is poly(n-butyl acrylate), poly(isooctyl acrylate), poly(2-octyl acrylate), poly(isobornyl acrylate), or poly(2-ethylhexyl acrylate).

Embodiment 24B is the adhesive article of any one of embodiments 1B to 23B, wherein the (meth)acrylic-based triblock copolymer A-B-A has a number average molecular weight ($M_n$) in a range of 25 to 150 kDaltons.

Embodiments 25B is the adhesive article of any one of embodiments 1B to 24B, wherein the (meth)acrylic-based diblock copolymer C-D has a number average molecular weight ($M_n$) in a range of 25 to 100 kDaltons.

Embodiment 26B is the adhesive article of any one of embodiments 1B to 25B, wherein the adhesive composition leaves no adhesive residue upon removal after being adhered to skin for 24 hours.

Embodiment 27B is the adhesive article of any one of embodiments 1B to 26B, wherein the electron beam radiation is in a range of 1 to 20 Mrads and/or the gamma ray radiation is in a range of 10 to 200 kilograys.

Embodiment 28B is the adhesive article of any one of embodiments 1B to 27B, wherein the substrate is a backing layer.

Embodiment 29B is the adhesive article of any one of embodiments 1B to 28B, wherein the backing layer comprises a polymeric material.

Embodiment 30B is the adhesive article of any one of embodiments 1B to 29B, wherein the adhesive article further comprises a pharmaceutical agent.

Embodiment 31B is the adhesive article of embodiment 30B, wherein the pharmaceutical agent is on a second major surface of the adhesive composition layer opposite the substrate.

Embodiment 32B is the adhesive article of any one of embodiments 1B to 31B, wherein a (the) second major surface of the adhesive composition layer that is opposite the first major surface of the adhesive composition layer is adhered to a biological surface.

Embodiment 33B is the adhesive article of embodiment 31B, wherein the biological surface is skin.

Embodiment 34B is the adhesive article of any one of embodiments 1B to 33B, wherein the adhesive article further comprises an adsorbent material positioned adjacent to but not covering an outer edge of a second (the) major surface of the adhesive composition layer.

Embodiment 35B is the adhesive article of embodiment 34B, wherein the adsorbent material is a foam, sponge, or hydrocolloid.

Embodiment 36B is the adhesive article of any one of embodiments 1B to 35B, wherein the adhesive article is a wound dressing.

Embodiment 37B is the adhesive article of any one of embodiments 1B to 36B, wherein the adhesive article attaches a medical device or catheter to the skin of a human or animal.

Embodiment 1C is a method of making an adhesive article. The method includes providing an adhesive composition comprising a (meth)acrylic-based composition that includes a) 0 to less than 10 weight percent of a (meth)acrylic-based triblock copolymer A-B-A and b) greater than 90 to 100 weight percent of a (meth)acrylic-based (meth)acrylic-based diblock copolymer C-D. The weight percent amounts are based on a total weight of the (meth)acrylic-based composition. Each A block of the optional (meth)acrylic-based triblock copolymer A-B-A is a polymerized product of a first monomer composition comprising an alkyl methacrylate and the B block is a polymerized product of a second monomer composition comprising an alkyl acrylate. The optional (meth)acrylic-based triblock copolymer A-B-A contains 20 to 55 weight percent A blocks and 45 to 80 weight percent B block based on a total weight of the triblock copolymer A-B-A. The C block of the (meth)acrylic-based diblock copolymer C-D is a polymerized product of a third monomer composition comprising an alkyl methacrylate and the D block is a polymerized product of a fourth monomer composition comprising an alkyl acrylate. The (meth)acrylic-based diblock copolymer C-D contains 5 to 30 weight percent C block and 70 to 95 weight percent D block based on a total weight of the (meth)acrylic-based diblock copolymer C-D. The method further includes forming an adhesive composition layer adjacent to a substrate. The method still further includes exposing the adhesive composition layer to electron beam radiation and/or gamma ray radiation to crosslink the adhesive composition layer.

Embodiment 2C is the method of embodiment 1C, wherein the adhesive composition is any one of embodiments 1A to 27A.

Embodiment 3C is the method of embodiment 1C or 2C, wherein the electron beam radiation is in a range of 1 to 20 Mrads and/or the gamma ray radiation is in a range of 10 to 200 kilograys.

Embodiment 4C is the method of any one of embodiments 1C to 3C, wherein the substrate is a backing layer.

Embodiment 5C is the method of embodiment 4C, wherein the backing layer comprises a polymeric material.

Embodiment 6C is the method of any one of embodiments 1C to 5C, further comprising positioning an adsorbent material adjacent to but not covering an outer edge of a major surface of the adhesive composition layer opposite the substrate.

Embodiment 7C is the method of any one of embodiments 1C to 6C, wherein the adsorbent material is a foam, sponge, or hydrocolloid.

Embodiment 8C is the method of any one of embodiments 1C to 7C, further comprising adding a pharmaceutical agent to a (the) major surface of the adhesive composition layer opposite the substrate.

EXAMPLES

All parts, percentages, ratios, and the like used in the Examples are by weight unless indicated otherwise.

Test Methods

Glass Transition Temperature Test

A Dynamic Mechanical Analysis (DMA) test method was used to determine glass transition temperatures. An AR2000 parallel plate rheometer (TA Instruments of New Castle, Del., USA) was used to characterize the physical properties of each sample as a function of temperature. For each polymeric sample, approximately 0.2 grams of material was centered between 8 mm diameter parallel plates of the rheometer and compressed until the edges of the sample were uniform with the edges of the top and bottom plates. The furnace doors that surround the parallel plates and shafts of the rheometer were shut and the temperature was raised to 140° C. and held for 5 minutes. The temperature was then ramped from 140° C. to −80° C. at 3° C./min while the parallel plates were oscillated at a frequency of 1 Hz and a constant percent strain (0.4 percent). During the temperature ramp, the storage modulus (G'), loss modulus (G"), and tan delta (the ratio of G"/G') were recorded.

The glass transition temperature, $T_g$, of the materials was determined by plotting tan delta versus temperature. The maximum point (point where the slope is zero) in the transition region between the glassy region and the rubbery region of the tan delta curve, if well defined, determines the $T_g$ of the material at that particular frequency.

Molecular Weight Measurement Test

The molecular weight distribution of the compounds was characterized using conventional gel permeation chroma-

TABLE 1

| Materials | |
| --- | --- |
| Abbreviation | Description and Source |
| LA2330 | A (meth)acrylic triblock copolymer A-B-A, where A is poly(methyl methacrylate) ("PMMA") and B is poly(n-butyl acrylate) ("PBA"), that is commercially available under the trade designation "KURARITY LA2330" from Kuraray America Inc., Houston, TX, USA. The PMMA content is believed to be approximately 24 weight percent based on a total weight of the copolymer. The number average molecular weight ($M_n$) is 97.5 kDaltons and the weight average molecular weight ($M_w$) is 105.3 kDaltons, as determined by gel permeation chromatography. |
| LA4285 | A (meth)acrylic triblock copolymer A-B-A, where A is PMMA and B is PBA, that is commercially available under the trade designation "KURARITY LA4285" from Kuraray America, Inc., Houston, TX, USA. The PMMA content is believed to be approximately 51 weight percent based on a total weight of the copolymer. The number average molecular weight is 48 kDaltons, and the weight average molecular weight is 57 kDaltons, as determined by gel permeation chromatography. |
| LA2140 | A (meth)acrylic triblock copolymer A-B-A, where A is PMMA and B is PBA, that is commercially available under the trade designation "KURARITY LA2140" from Kuraray America Inc. Houston, TX, USA. The PMMA content is believed to be approximately 24 weight percent based on a total weight of the copolymer. The number average molecular weight is 60 kDaltons and the weight average molecular weight is 66 kDaltons, as determined by gel permeation chromatography. |
| LA1114 | A (meth)acrylic diblock copolymer C-D, where C is PMMA and D is PBA, that is commercially available under the trade designation "KURARITY LA1114" from Kuraray America Inc., Houston, TX, USA. The PMMA content is believed to be approximately 7 weight percent based on a total weight of the copolymer. The weight average molecular weight is 60 kDaltons, as determined by gel permeation chromatography. |
| S540 | A phenol-modified copolymer of styrene and alpha methyl styrene tackifier resin that is commercially available under the trade designation SYLVARES 540 from Arizona Chemical, Jacksonville, FL, USA. |
| TP115P | A terpene phenolic tackifier resin that is commercially available under the trade designation SYLVARES TP115P from Arizona Chemical, Jacksonville, FL, USA. |
| Backing | A backing having two layers heat bonded together with the first layer being a nonwoven polyester material and the second layer being a thermoplastic polyester elastomer. The second layer has a three second Shore D hardness of 32 as tested per ISO 868 and a melting temperature of approximately 212° C. | tography (GPC). The GPC instrumentation, which was obtained from Waters Corporation (Milford, Mass., USA), included a high pressure liquid chromatography pump, an auto-sampler, a UV detector, and a refractive index detector. The chromatograph was equipped with two 5 micron PLgel MIXED-D columns that are available from Varian Inc. (Palo Alto, Calif., USA).

Samples of polymeric solutions were prepared by dissolving polymer or dried polymer samples in tetrahydrofuran at a concentration of 0.5 percent (weight/volume) and by filtering through a 0.2 micron polytetrafluoroethylene filter that is available from VWR International (West Chester, Pa., USA).

The resulting samples were injected into the GPC and eluted at a rate of 1 milliliter per minute through the columns maintained at 35° C. The system was calibrated with polystyrene standards using a linear least squares analysis fit to establish a calibration curve. The weight average molecular weight ($M_w$), the number average molecular weight ($M_n$) and the polydispersity index ($M_w/M_n$) were calculated for each sample against this standard calibration curve.

180° Peel Adhesion Test

Peel adhesion, at an angle of 180° and at room temperature (approximately 74° F. (23° C.)), was determined generally according to ASTM D3330 Method E. Tape samples measuring 1 inch (2.54 cm) wide were cut from the coated sample (i.e., the adhesive composition coated on the backing). Stainless steel test panels were cleaned with reagent grade n-heptane followed by methyl ethyl ketone using a clean lint-free absorbent tissue. The release liner was removed and the tape sample was rolled down onto a stainless steel panel, with the adhesive in contact with the panel, using a 4.5 pound (2.0 kg) roller and two passes in each direction. The sample was allowed to dwell for 10-20 minutes before peeling at a rate of 12 inches (30 cm) per minute using an IMASS 2000 Slip/Peel Tester (available from Instrumentors, Inc., Strongsville, Ohio, USA) with data acquired for five seconds. Two tape samples were evaluated and the average value of the two was reported in ounces force per inch.

Shear Strength Test

Shear strength, at room temperature (approximately 74° F. (23° C.)), was determined generally according to ASTM D3654 Method A. Stainless steel test panels were cleaned with reagent grade n-heptane followed by methyl ethyl ketone using clean lint-free absorbent tissue. Tape samples measuring 0.5 inch (1.27 cm) wide were cut from the coated samples. The release liner was removed and the tape sample was rolled down onto a cleaned stainless steel panel, with the adhesive in contact with the panel, using a 4.5 pound (2.0 kg) roller and two passes in each direction. A hook was attached to the end of the tape not in contact with the panel and the portion of the sample adhered to the panel was trimmed such that the area of the tape adhered to the panel measured either 0.5 inch (1.27 cm) by 0.5 inch (1.27 cm) or 0.5 inch (1.27 cm) by 1 inch (2.54 cm), as specified in the tables. The sample was allowed to dwell for at least one minute prior to placing the test panel in the test stand in a vertical position with the hook hanging down. A 250 gram mass was applied to the hook. Two to three tape samples were evaluated for failure times and the average value was reported in minutes.

Adhesion to Skin Test

Tape samples measuring 1.9 cm by 5.1 cm were cut from the coated samples. The release liner was removed from the tape sample and it was centered and adhered to the palm side of a forearm of a healthy human volunteer. Visual assessments of tape edge lift were recorded after 24 hours of wear. Visual assessment was used to evaluate the tape edge lift characteristics of the tape sample. An edge lift of 25 percent or less of the sample area (entire sample area) is desired.

After assessing tape edge lift, the samples were peeled from the skin at an angle of 180 degrees and a rate of approximately 90 inches (229 cm) per minute. The presence of residue was noted using the following visual assessment scale:

Residue:

0=0 percent of area under the sample has left residue on skin

1=1 to 25 percent of area under the sample has left residue on skin

2=26 to 50 percent of area under the sample has left residue on skin

3=51 to 75 percent of area under the sample has left residue on skin

4=76 to 100 percent of area under the sample has left residue on skin

All the tape samples included in the examples below exhibited a residue rating of 0 or 1.

EXAMPLES AND COMPARATIVE EXAMPLES

Various adhesive compositions were prepared that contained a (meth)acrylic-based composition with a (meth)acrylic-based diblock copolymer and an optional (meth)acrylic-based triblock copolymer. In some of these adhesive compositions, tackifiers were combined with the (meth)acrylic-based composition. The block copolymers (and tackifier, if included) were dissolved in toluene in the amounts specified in Table 2 to Table 4 below to provide 40 weight percent solid solutions. These solutions were knife coated on the Backing and dried in an oven at 70° C. for 10 minutes. The final thickness of the dried adhesive layer was between 30 and 50 micrometers. Next, a silicone-treated polyester release liner was laminated onto the adhesive layer for some of the resulting tape samples (i.e., those that were not treated with electron beam radiation). The remaining tape samples were treated with electron beam radiation and then a silicone-treated polyester release liner was placed over the electron beam treated adhesive layer.

Some tape samples (as indicated in the tables below) were exposed to electron beam radiation to crosslink the adhesive layer. Electron beam irradiation was carried out using a Model CB-300 electron beam generating apparatus (available from Energy Sciences, Inc., Wilmington, Mass., USA) with a nitrogen purge to reduce atmospheric oxygen concentration below 500 ppm, and at a speed of 20 feet (6.1 meters) per minute. A polyester support film was used as a conveyor belt to move the tape samples through the irradiation chamber. The adhesive side of the tape samples was irradiated. The accelerating voltage applied was 280 kV. Electron beam doses used are specified in the tables below.

All tape samples were conditioned in a constant temperature (23° C.) and humidity room (50 percent relative humidity) for at least 24 hours before testing.

Examples 1 to 8 (EX-1 to EX-8) and Comparative Examples 1 to 5 (CE-1 to CE-5) had the compositions and test results as summarized in Table 2. All Examples and Comparative Examples in Table 2 exhibited a cohesive failure mode for both the peel adhesion test and the static shear test. Further, all Examples and Comparative Examples in Table 2 exhibited an edge lift of 25 percent or less. The static shear test results for Table 2 are based on tape samples having an area of 0.5 inch×0.5 inch (whereas the static shear test results for Tables 3 and 4 are based on tape samples having an area of 0.5 inch×1.0 inch).

TABLE 2

EX-1 to EX-8 and CE-1 to CE-5

| | (Meth)acrylic-based Composition (wt. %) | | Electron Beam | Adhesion to Steel | | Adhesion to Skin |
|---|---|---|---|---|---|---|
| | | | | Peel Adhesion | Static | |
| Sample | LA2330 (Triblock) | LA1114 (Diblock) | Dose (Mrad) | Strength (oz/inch) | Shear (min) | Residue (0-4) |
| CE-1 | 0 | 100 | 0 | 11.3 | 2 | 4 |
| EX-1 | | | 12 | 28.2 | 58 | 0 |
| EX-2 | | | 14 | 32.2 | 165 | 0 |
| CE-2 | 4 | 96 | 0 | 15.5 | 4 | 4 |
| EX-3 | | | 6 | 20.3 | 28 | 1 |
| EX-4 | | | 8 | 23.2 | 59 | 0 |
| EX-5 | | | 10 | 25.9 | 160 | 0 |
| CE-3 | 8 | 92 | 0 | 17.3 | 12 | 3 |
| EX-6 | | | 2 | 18.5 | 21 | 1 |
| EX-7 | | | 4 | 20.6 | 63 | 0 |
| EX-8 | | | 6 | 23.3 | 99 | 0 |
| CE-4 | 10 | 90 | 0 | 20.6 | 23 | 2 |
| CE-5 | 12 | 88 | 0 | 20.3 | 122 | 1 |

Examples EX-9 to EX-10 and Comparative Examples CE-6 to CE-7 included tackifier additives (in parts per hundred ("pph") relative to the 100 parts (meth)acrylic-based compositions). The compositions and test results are summarized in Table 3. All Examples and Comparative Examples in Table 3 exhibited a cohesive failure mode for both the peel adhesion test and the static shear test. Further, all Examples and Comparative Examples in Table 3 exhibited an edge lift of 25 percent or less. The static shear test results for Table 3 (and Table 4) are based on tape samples having an area of 0.5 inch×1.0 inch (rather than 0.5 inch×0.5 inch as in Table 2).

TABLE 3

EX-9 to EX-10 and CE-6 to CE-7

| | (Meth)acrylic-based Composition (wt. %) | | Tackifer | | Electron Beam | Adhesion to Steel | | Adhesion to Skin |
|---|---|---|---|---|---|---|---|---|
| | | | Amount (pph of | | | Peel Adhesion | Static | |
| Sample | LA2330 (Triblock) | LA1114 (Diblock) | (Meth)acrylic Composition) | Tackifier | Dose (Mrad) | Strength (oz/inch) | Shear (min) | Residue (0-4) |
| CE-6 | 8 | 92 | 20 | S540 | 0 | 28.7 | 29 | 3 |
| EX-9 | | | | | 2 | 29.7 | 41 | 0 |
| CE-7 | 8 | 92 | 20 | TP115 | 0 | 26.4 | 56 | 3 |
| EX-10 | | | | | 4 | 29.5 | 92 | 0 |

Examples EX-11 to EX-12 and Comparative Examples CE-8 to CE-9 included other grades of the (meth)acrylic-based triblock copolymer. The compositions and test results are summarized in Table 4. All Examples and Comparative Examples in Table 4 exhibited a cohesive failure mode for both the peel adhesion test and the static shear test. Further, all Examples and Comparative Examples in Table 4 exhibited an edge lift of 25 percent or less. The static shear test results for Table 4 (and Table 3) are based on tape samples having an area of 0.5 inch×1.0 inch (rather than 0.5 inch×0.5 inch as in Table 2).

TABLE 4

EX-11 to EX-12 and CE-8 to CE-9

| | (Meth)acrylic-based Composition (wt. %) | | | Electron Beam | Adhesion to Steel | | Adhesion to Skin |
|---|---|---|---|---|---|---|---|
| | Triblock | | LA1114 | | Peel Adhesion | Static | |
| Sample | type | Triblock | (Diblock) | Dose (Mrad) | Strength (oz/inch) | Shear (min) | Residue (0-4) |
| CE-8 | LA4285 | 8 | 92 | 0 | 12.1 | 18 | 4 |
| EX-11 | | | | 6 | 21.1 | 51 | 0 |
| CE-9 | LA2140 | 8 | 92 | 0 | 17.8 | 47 | 3 |
| EX-12 | | | | 4 | 23.9 | 154 | 0 |

We claim:

1. An adhesive article comprising:
   a substrate; and
   an adhesive composition layer having a first major surface attached to the substrate, wherein the adhesive composition layer comprises a crosslinked polymeric product of a reaction mixture comprising
   a) a (meth)acrylic-based composition comprising
      1) 0 to less than 10 weight percent of a (meth)acrylic-based triblock copolymer A-B-A based on a total weight of the (meth)acrylic-based composition, wherein
         each A block is a polymerized product of a first monomer composition comprising an alkyl methacrylate;
         the B block is a polymerized product of a second monomer composition comprising an alkyl acrylate;
         the (meth)acrylic-based triblock copolymer A-B-A having 20 to 55 weight percent A blocks and 45 to 80 weight percent B block based on a total weight of the (meth)acrylic-based triblock copolymer A-B-A; and
      2) greater than 90 to 100 weight percent of a (meth)acrylic-based diblock copolymer C-D based on the total weight of the (meth)acrylic-based composition, wherein
         the C block is a polymerized product of a third monomer composition comprising an alkyl methacrylate;
         the D block is a polymerized product of a fourth monomer composition comprising an alkyl acrylate; and
         the (meth)acrylic-based diblock copolymer C-D having 5 to 30 weight percent C block and 70 to 95 weight percent D block based on a total weight of the (meth)acrylic-based diblock copolymer C-D; and
   b) electron beam radiation and/or gamma ray radiation, wherein the reaction mixture is free of a chemical crosslinking agent; and
   an absorbent material positioned adjacent to but not covering an outer edge of a second major surface of the adhesive composition layer opposite the substrate.

2. The adhesive article of claim 1, wherein the substrate is a backing layer.

3. The adhesive article of claim 1, further comprising a pharmaceutical agent.

4. The adhesive article of claim 1, wherein the adhesive article is adhered to skin.

5. The adhesive article of claim 1, wherein each A block has a glass transition temperature equal to at least 50° C. and wherein the B block has a glass transition temperature no greater than 20° C. when measured using Dynamic Mechanical Analysis.

6. The adhesive article of claim 1, wherein the adhesive composition further comprises an additive selected from a tackifier, plasticizer, filler, or a combination thereof.

7. The adhesive article of claim 1, wherein the A blocks of the (meth)acrylic-based triblock copolymer A-B-A and the C block of the (meth)acrylic-based diblock copolymer C-D comprise the same alkyl methacrylate having a glass transition temperature as a homopolymer that is at least 50° C. when measured using Dynamic Mechanical Analysis.

8. The adhesive article of claim 1, wherein the B block of the (meth)acrylic-based triblock copolymer A-B-A and the D block of the (meth)acrylic-based diblock copolymer comprise the same alkyl acrylate having a glass transition temperature as a homopolymer that is no greater than 20° C. when measured using Dynamic Mechanical Analysis.

9. The adhesive article of claim 1, wherein the A blocks of the (meth)acrylic-based triblock copolymer A-B-A and the C block of the C-D (meth)acrylic-based diblock copolymer are poly(methyl methacrylate) and wherein the B block of the (meth)acrylic-based triblock copolymer A-B-A and the D block of the C-D (meth)acrylic-based diblock copolymer are both a poly(n-butyl acrylate), poly(isooctyl acrylate), poly(2-octyl acrylate), poly(isobornyl acrylate), or poly(2-ethylhexyl acrylate).

10. The adhesive article of claim 1, wherein the (meth)acrylic-based triblock copolymer A-B-A has a number average molecular weight ($M_n$) in a range of 25 to 150 kDaltons and wherein the (meth)acrylic-based diblock copolymer C-D has a number average molecular weight ($M_n$) in a range of 25 to 100 kDaltons.

11. The adhesive article of claim 1, wherein the adhesive composition comprises 70 to 100 weight percent of the (meth)acrylic-based composition and 0 to 30 weight percent of an additive selected from a tackifier, plasticizer, filler, or combination thereof.

* * * * *